(12) United States Patent
Wojczak et al.

(10) Patent No.: US 12,263,261 B2
(45) Date of Patent: Apr. 1, 2025

(54) UV SANITIZING LIGHT MODULE AND CONTAINER SYSTEM

(71) Applicant: CONAIR CORPORATION, Stamford, CT (US)

(72) Inventors: Sophia Wojczak, Harrison, NY (US); Paul James Carrubba, Baldwin, NY (US); Daniel Bishop, Monroe, CT (US)

(73) Assignee: CONAIR LLC, Stamford, CT (US)

( * ) Notice: Subject to any disclaimer, the term of this patent is extended or adjusted under 35 U.S.C. 154(b) by 116 days.

(21) Appl. No.: 16/938,270

(22) Filed: Jul. 24, 2020

(65) Prior Publication Data

US 2022/0023456 A1  Jan. 27, 2022

(51) Int. Cl.
*A61L 2/10* (2006.01)
*A61L 2/26* (2006.01)

(52) U.S. Cl.
CPC ........ *A61L 2/10* (2013.01); *A61L 2/26* (2013.01); *A61L 2202/14* (2013.01); *A61L 2202/16* (2013.01)

(58) Field of Classification Search
CPC .......... A61L 2/10; A61L 2/24; A61L 2202/14; A61L 2202/16; A61L 2202/23; A61L 2/26
See application file for complete search history.

(56) References Cited

U.S. PATENT DOCUMENTS

| | | | |
|---|---|---|---|
| 4,309,388 A | 1/1982 | Tenney et al. | |
| 4,806,770 A | 2/1989 | Hylton et al. | |
| 4,869,390 A * | 9/1989 | Kennedy | A47G 19/2205 220/709 |
| 5,597,482 A * | 1/1997 | Melyon | C02F 1/325 210/260 |
| 6,461,568 B1 | 10/2002 | Eckhardt | |
| 6,753,537 B2 | 6/2004 | Woo | |
| 7,390,417 B2 | 6/2008 | Kuhlmann et al. | |
| 7,560,706 B1 | 7/2009 | Castelluccio | |
| 8,481,970 B2 | 7/2013 | Cooper et al. | |
| 8,964,405 B2 | 2/2015 | La Porte et al. | |
| 9,006,680 B2 | 4/2015 | Bettles et al. | |
| 9,045,358 B2 * | 6/2015 | Greuel | C02F 1/325 |
| 9,066,987 B2 | 6/2015 | Bettles et al. | |
| 9,265,849 B2 | 2/2016 | Kerr | |

(Continued)

FOREIGN PATENT DOCUMENTS

CN  102361823 A  2/2012
CN  206437356 U *  8/2017

(Continued)

OTHER PUBLICATIONS

Corresponding PCT Application No. PCT/US2021/041218 International Search Report and Written Opinion dated Nov. 3, 2021.

*Primary Examiner* — David E Smith
(74) *Attorney, Agent, or Firm* — Grogan, Tuccillo & Vanderleeden LLP

(57) ABSTRACT

A sanitizing module includes a housing having an open end, and at least one ultraviolet light emitting element within the housing and being configured to emit ultraviolet light out of the housing through the open end. The housing is configured for removable connection to a container having an interior receiving space such that connection of the housing to the container encloses the interior receiving space of the container.

17 Claims, 26 Drawing Sheets

(56) References Cited

U.S. PATENT DOCUMENTS

| | | | |
|---|---|---|---|
| 9,339,576 B2 | 5/2016 | LaPorte et al. | |
| 9,717,809 B2 | 8/2017 | Martz et al. | |
| 9,789,220 B2 | 10/2017 | Pugh et al. | |
| 9,801,955 B2* | 10/2017 | Thompson | A61K 49/0017 |
| 9,801,965 B2* | 10/2017 | Bettles | A61L 2/10 |
| 9,839,707 B2 | 12/2017 | Won | |
| 10,258,715 B1* | 4/2019 | Collins | A23L 3/28 |
| 10,549,001 B2 | 2/2020 | Martz et al. | |
| 2005/0176479 A1 | 8/2005 | Bae et al. | |
| 2005/0258108 A1* | 11/2005 | Sanford | C02F 1/325 |
| | | | 210/748.11 |
| 2007/0201220 A1* | 8/2007 | Ulicny | B65D 23/00 |
| | | | 362/101 |
| 2007/0274879 A1 | 11/2007 | Millikin | |
| 2008/0067419 A1 | 3/2008 | Shih | |
| 2008/0223739 A1* | 9/2008 | Thompson | A47G 19/2227 |
| | | | 206/217 |
| 2009/0114854 A1 | 5/2009 | Garcia et al. | |
| 2010/0133285 A1* | 6/2010 | Schepen | B65D 43/0229 |
| | | | 220/780 |
| 2011/0049391 A1* | 3/2011 | Yang | A61L 2/10 |
| | | | 250/492.1 |
| 2012/0006995 A1* | 1/2012 | Greuel | A61L 2/10 |
| | | | 250/455.11 |
| 2012/0067749 A1* | 3/2012 | Coombes | A47J 47/00 |
| | | | 220/500 |
| 2012/0074334 A1 | 3/2012 | Milligan | |
| 2013/0004367 A1 | 1/2013 | Roberts | |
| 2013/0063922 A1 | 3/2013 | La Porte et al. | |
| 2014/0202948 A1* | 7/2014 | Li | C02F 1/002 |
| | | | 210/251 |
| 2014/0319374 A1 | 10/2014 | Chandler | |
| 2015/0144575 A1 | 5/2015 | Hawkins, II | |
| 2016/0256590 A1 | 9/2016 | Taghipour | |
| 2017/0086560 A1 | 3/2017 | Pires et al. | |
| 2017/0172852 A1 | 6/2017 | McBean et al. | |
| 2018/0036444 A1 | 2/2018 | Bettles et al. | |
| 2018/0104367 A1 | 4/2018 | Bettles et al. | |
| 2019/0262493 A1 | 8/2019 | Collins et al. | |
| 2020/0254122 A1* | 8/2020 | Starkweather | A61L 2/28 |
| 2021/0330827 A1* | 10/2021 | Lucio | A61L 2/26 |

FOREIGN PATENT DOCUMENTS

| | | |
|---|---|---|
| CN | 201830556961 S | 2/2019 |
| CN | 210184757 U | 3/2020 |
| CN | 201921201431 U | 3/2020 |
| JP | H11318566 A | 11/1999 |
| KR | 20130135675 A | 12/2013 |
| KR | 20170105542 A * | 9/2017 |

* cited by examiner

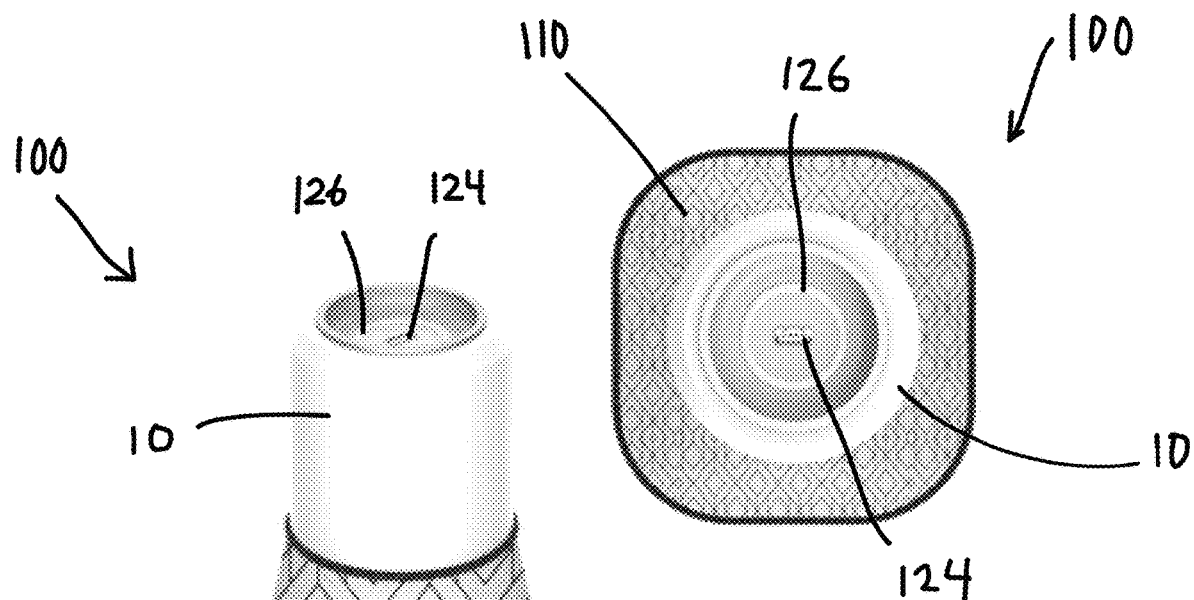
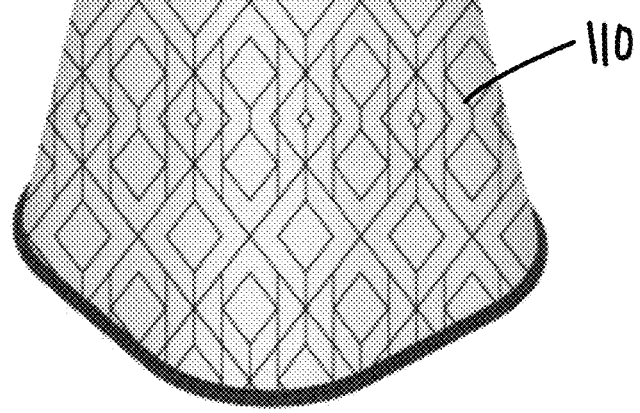
FIG. 5
FIG. 6

UV SANITIZING LIGHT MODULE AND CONTAINER SYSTEM

FIELD OF THE INVENTION

The present invention relates generally to sanitizing devices and, more particularly, to a sanitizing module and container system for the sanitization of personal items using ultraviolet light.

BACKGROUND OF THE INVENTION

The concern over the spread of contagions such as bacteria and viruses through physical contact with contaminated items has always been present, but has been heightened by the outbreak of COVID-19. Indeed, with the outbreak of COVID-19, the need and desire to sanitize high touch items such as mobile telephones, keys, small toys, and personal hygiene devices and items such as hairbrushes and cosmetics, among others, has only increased.

It has heretofore been difficult to easily and efficiently clean such items to a sanitary condition, however. For example, electronic elements of mobile phones and other items cannot be safely exposed to water, including alcohol based solutions. Some materials, such as silicones, cannot be exposed to particular cleaning chemicals. In addition, items with complex shapes (including small nooks and crevices) are particularly difficult to clean with wipes or sanitizing solutions.

In view of the above, there is a need for an ultraviolet sanitizing light module and container system for easily and efficiently sanitizing high touch personal items such as mobile phones, keys, cosmetics and the like.

SUMMARY OF THE INVENTION

It is an object of the present invention to provide a sanitizing module.

It is another object of the present invention to provide an ultraviolet sanitizing light module for sanitizing personal items.

It is another object of the present invention to provide an ultraviolet sanitizing light module that can be used with a plurality of different containers.

It is another object of the present invention to provide a container system for sanitizing personal items using ultraviolet light.

These and other objects are achieved by the present invention.

According to an embodiment of the present invention, a sanitizing module includes a housing having an open end, and at least one ultraviolet light emitting element within the housing and being configured to emit ultraviolet light out of the housing through the open end. The housing is configured for removable connection to a container having an interior receiving space such that connection of the housing to the container encloses the interior receiving space of the container.

According to another embodiment of the present invention, a sanitizing container system includes a sanitizing module having a housing and at least one ultraviolet light emitting element within the housing, and a container having an open end and an interior receiving space, the open end providing access to the interior receiving space. The sanitizing module is configured to be removably connected to the open end of the container to enclose the interior receiving space, and the at least one ultraviolet light emitting element is configured to emit ultraviolet light from the housing and into the interior receiving space of the container when the sanitizing module is connected to the container.

According to yet another embodiment of the present invention, a method of sanitizing an object includes providing a sanitizing module having a housing and at least one ultraviolet light emitting element within the housing, providing a container having an open end and an interior receiving space, the open end providing access to the interior receiving space, and connecting the sanitizing module to the open end of the container to enclose the interior receiving space. The at least one ultraviolet light emitting element is configured to emit ultraviolet light from the housing and into the interior receiving space of the container when the sanitizing module is connected to the container.

BRIEF DESCRIPTION OF THE DRAWINGS

The present invention will be better understood from reading the following description of non-limiting embodiments, with reference to the attached drawings, wherein below:

FIG. 5 is a perspective view of a container system having a UV sanitizing light module, according to another embodiment of the present invention.

FIG. 6 is a top plan view of the container system of FIG. 5.

DETAILED DESCRIPTION OF THE PREFERRED EMBODIMENT

Figure 4:
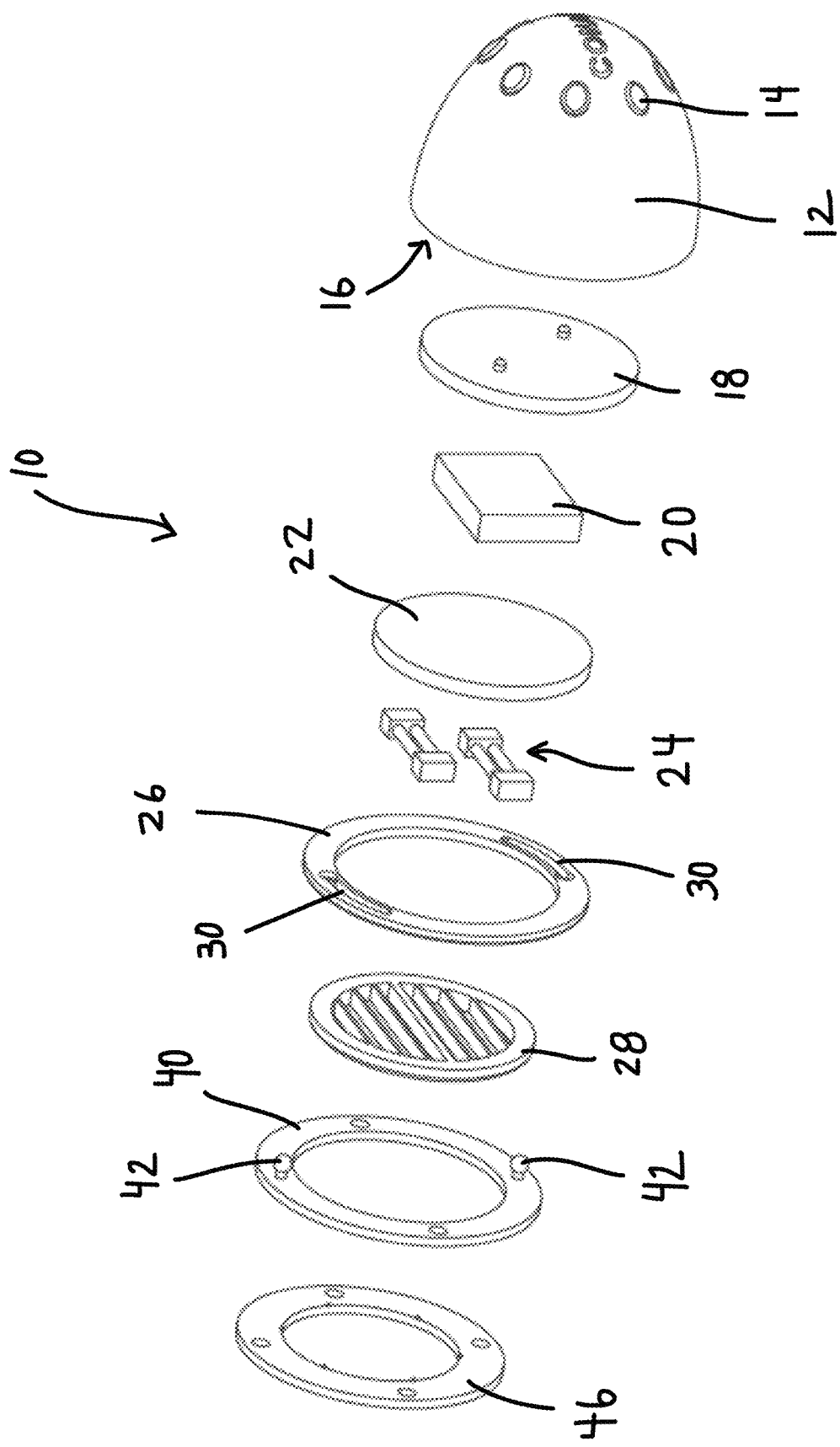
FIG. 4 is an exploded, perspective view of the UV sanitizing light module of FIG. 1.
Figure 7:
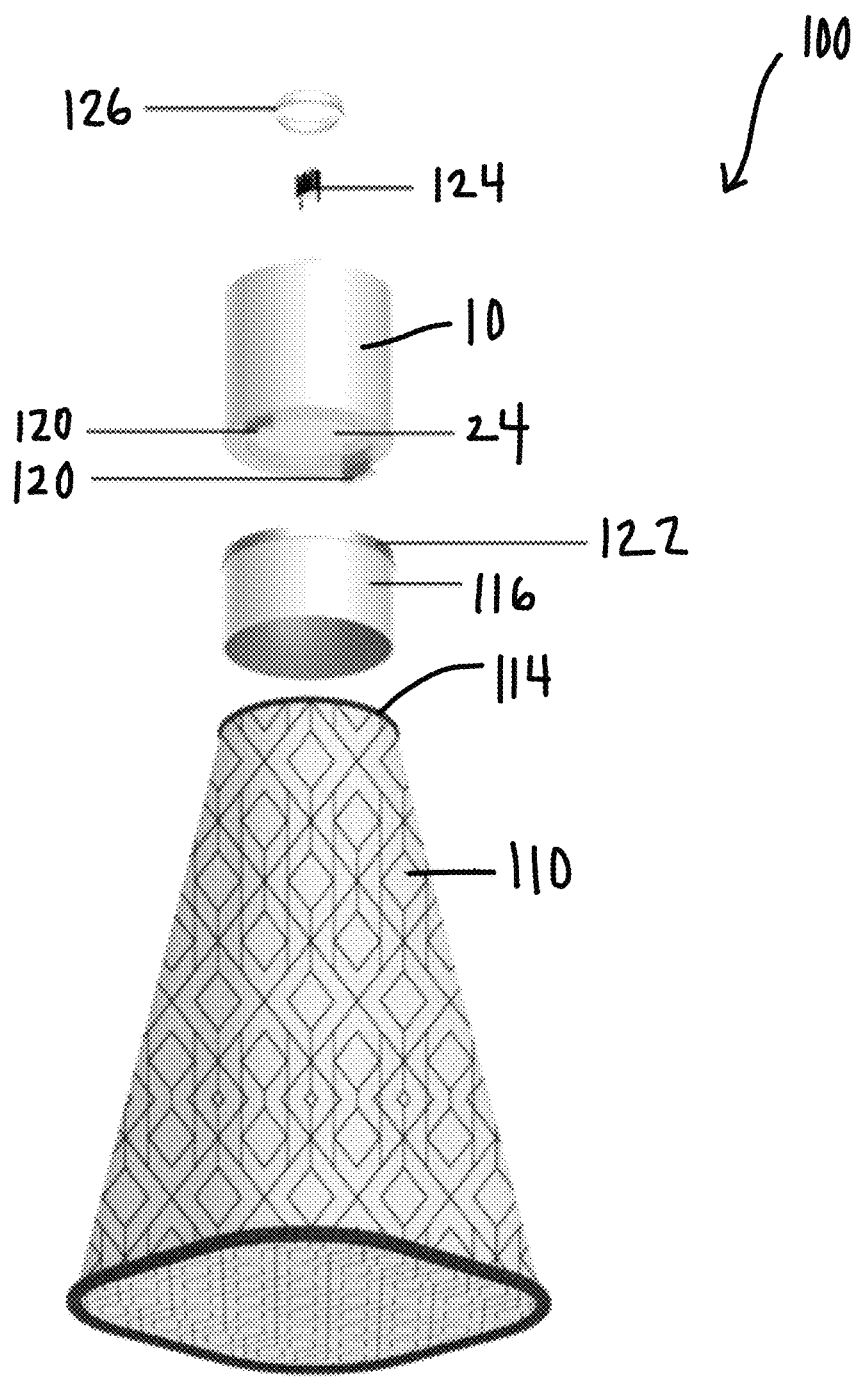
FIG. 7 is an exploded, perspective view of the container system of FIG. 5.

With reference to FIGS. 1-4, an ultraviolet sanitizing light module 10 according to an embodiment of the present invention is illustrated. The ultraviolet sanitizing light module 10 includes a housing 12 having an open end 14 and a plurality of protrusions 16 or gripping members formed on an exterior surface thereof. While the housing 12 is illustrated as having a dome shape, it is contemplated that the housing 12 may instead have a cylindrical, rectangular, hexagonal, octagonal or other shape without departing from the broader aspects of the invention. As further shown therein, the module 10 also includes a first partition or board 18, an energy storage module, e.g., a battery 20, a second partition or board 22, and at least one, and preferably a plurality of, light emitting elements 24, all positioned within the housing 12. The light emitting elements 24 are electrically connected to the battery for receiving power therefrom, as discussed in detail below. As shown in FIG. 4, the battery 20 is preferably sandwiched between the partitions 18, 20 within the housing 12.

Figure 1:
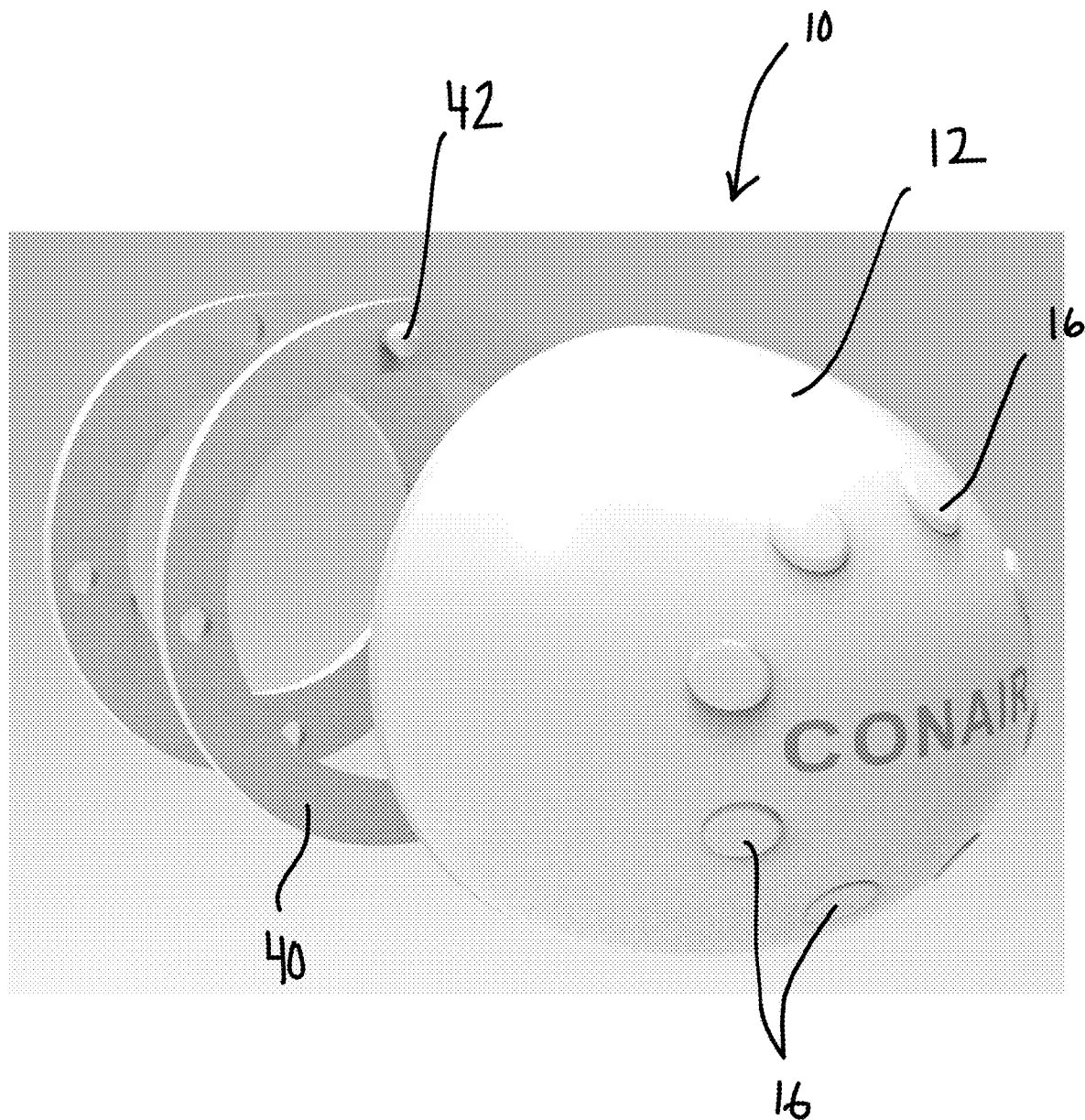
FIG. 1 is a top, perspective view of a UV sanitizing light module according to an embodiment of the present invention.
Figure 2:
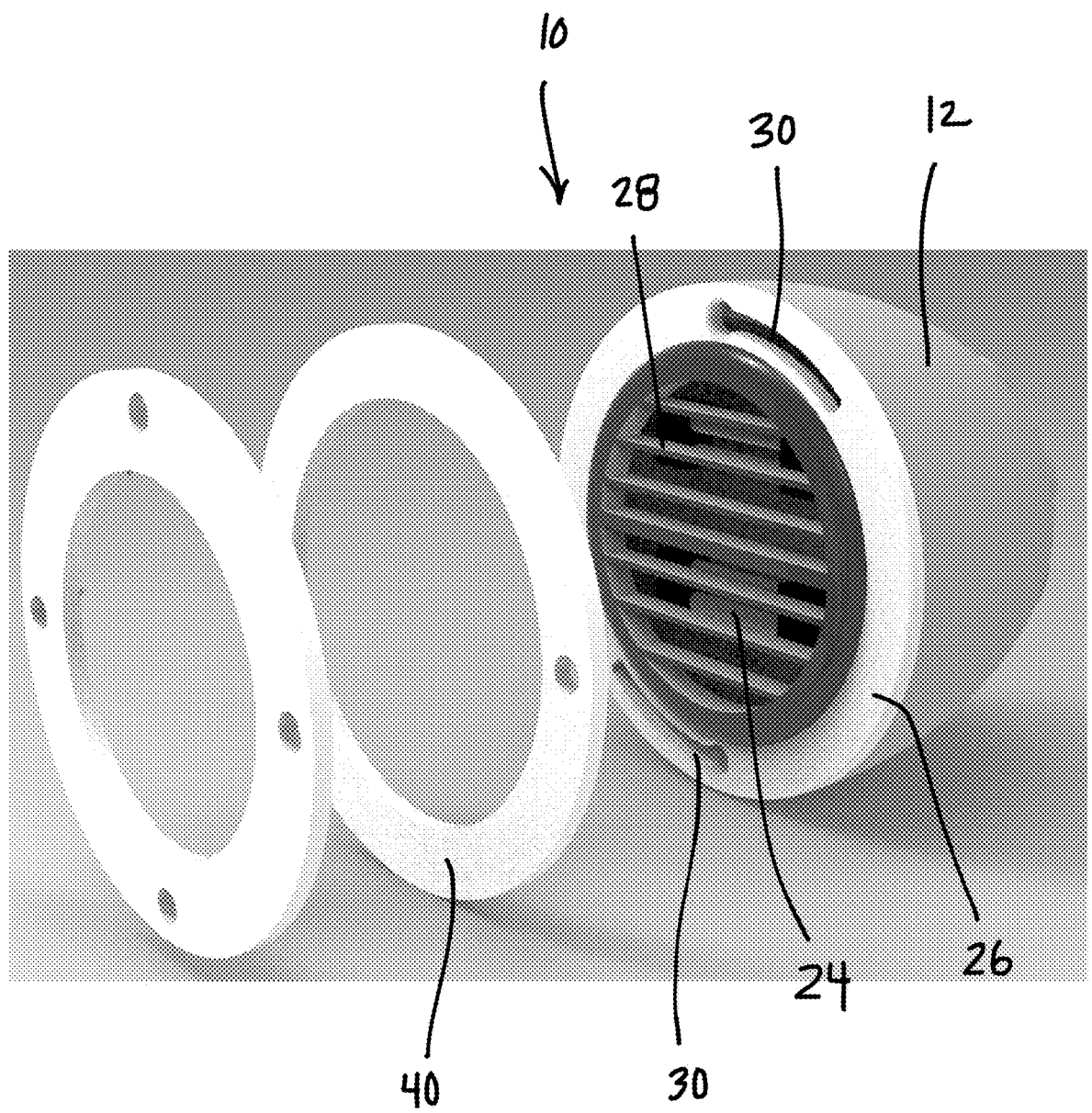
FIG. 2 is a bottom, perspective view the UV sanitizing light module of FIG. 1.
Figure 3:
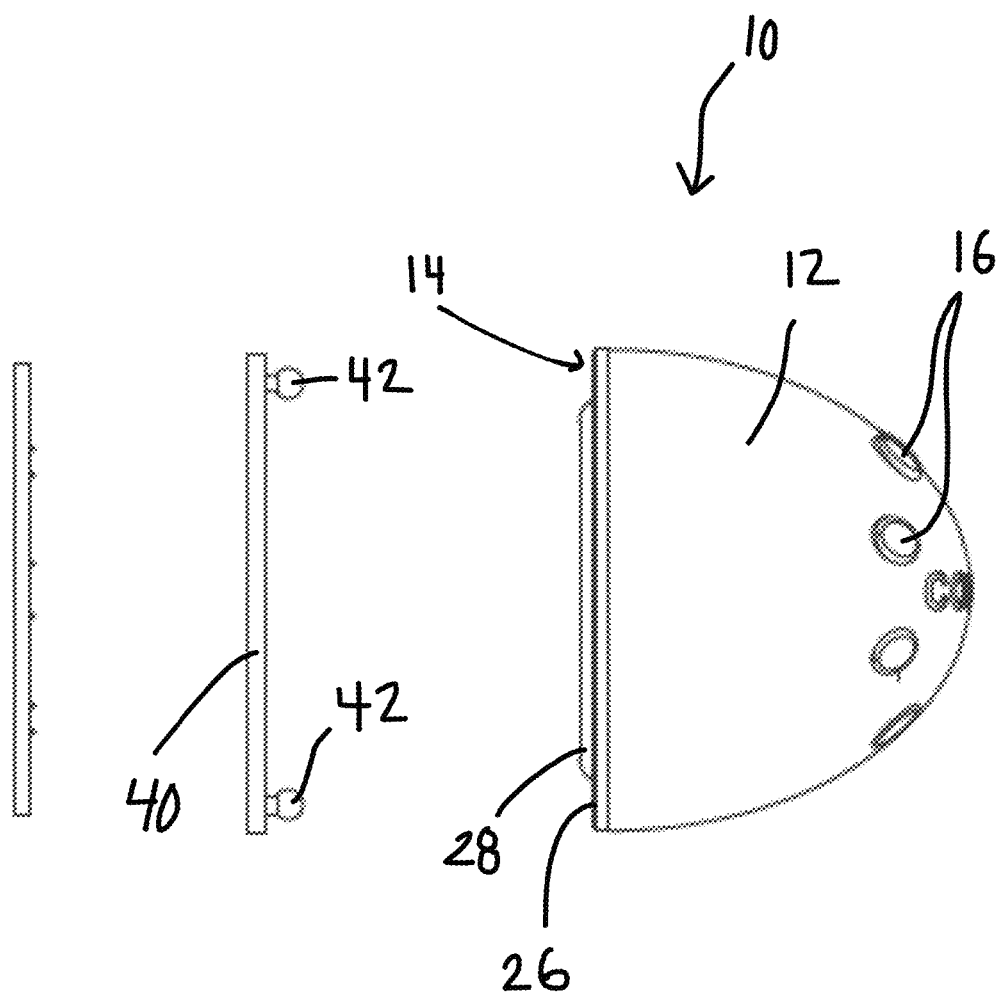
FIG. 3 is a side elevational view of the UV sanitizing light module of FIG. 1.

As best shown in FIGS. 2 and 4, the module 10 further includes an attachment/locking plate 26 received on the open end 14 of the housing. The attachment plate 26 is annular in shape and receives therein a grill 28 through which light emitted by the light emitting elements 24 can exit the housing 12. While the attachment/locking plate 26 and grill 28 are illustrated as separate components, it is contemplated that they may be formed as a single component configured for attachment to the open end 14 of the housing, such as via adhesive, welding or fasteners.

In an embodiment the light emitting elements 24 are ultraviolet light emitting diodes (UV LEDs) and are positioned within the housing adjacent to the grill 28. The UV LEDs may emit light in at least one of the UV-A (about 315 to about 415 nanometers), UV-B (about 280 to about 315 nanometers) and/or UV-C (about 100 to about 280 nanometer) ranges. Preferably, the UV LEDs emit light having wavelengths ranging from about 100 nanometers to about 280 nanometers (i.e., UV-C), which has been shown to kill bacteria and inactivate viruses such as, for example, COVID-19 and influenza. The UV LEDs 24 may emit light continuously, in regular pulses, or in irregular pulses. In an embodiment, the intensity of the UV LEDs 24 may be sufficient to kill bacteria, mold, yeast, fungi, and certain viruses, in the manner disclosed hereinafter.

While the present invention discloses the use of UV LEDs, the present invention is not intended to be so limited in this regard. In particular, it is contemplated the UV light emitting elements may be any type of light emitting element known in the art configured to emit ultraviolet light including, for example, tube bulbs.

In an embodiment, the attachment/locking plate 26 on the open end of the housing 12 includes a first connection member for selective connection of the ultraviolet sanitizing light module 10 to a container via a corresponding second connection member associated with the container. For example, in an embodiment, the first connection member may include one or more, and preferably two, arcuate keyhole slots 30. With continued reference to FIGS. 1-4, and in connection with the above, the ultraviolet sanitizing light module 10 may further include an annular plate 40 having a pair of lugs 42 (second connection member) that are configured and positioned to be received by the keyhole slots 30 in the attachment/locking plate 26. Alternatively, the components may be reversed such that the annular plate 26 is formed with lugs, and the annular plate 40 may have keyhole slots for receiving the lugs.

In use, the annular plate 40 may be integrated with a container (e.g., via adhesive, fasteners or the like). The ultraviolet light sanitizing module 10 (i.e., the housing 12 and its associated components) may then be attached to the container through mating engagement of the second connection member (e.g., lugs 42) of the container with the first connection member (e.g., keyhole slots 30) on the housing 12. In particular, to connect the housing 12 to a container, the attachment/locking plate 26 is brought into registration with the annular plate 40 on the container (not shown) so that the lugs 42 are received in the enlarged portion of the keyhole slots 30. The container and/or housing 12 is then rotated so that the lugs 42 are received in the narrow portions of the keyhole slots 30, thereby connecting the housing 12 to the container. Removal of the module 10 may be effected by carrying out these steps in reverse order.

As also show therein, in an embodiment, the module 10 may also include a secondary annular plate 46 that may be utilized in conjunction with the annular plate 40 to outfit the annular plate 40 to a container. For example, in the case of a fabric container or bag, the fabric may be sandwiched and held between the annular plates 40, 46. As disclosed above, therefore, the annular plates 40, 46, and the second connecting member of the annular plate 40 are intended to be attached to or otherwise integrated with a container for receiving items to be sterilized. The UV sanitizing light module 10 (i.e., the housing 12 and all its components) can then be attached to the container in the manner described above to provide for selective sanitization of the items within the container.

While the connection mechanism has been hereinbefore disclosed and illustrated as being at least one keyhole slot and corresponding lugs, it is contemplated that other connection mechanisms such a magnetic couplings, bayonet connectors and the like may also be utilized without departing from the broader aspects of the invention. In an embodiment, the UV sanitizing light module 10 may also include a switch (not shown) that is intended to be activated when the connection mechanism is fully engaged (e.g., when the lugs 42 are fully seated within the distal ends of the keyhole slots 30. Upon actuation of the switch, the light emitting elements 24 are activated. Similarly, when the connection mechanism is disengaged (i.e., when the module 10 is removed from a container), the light emitting elements 24 are automatically deactivated. In an embodiment, the switch may be a mechanical switch or a magnetic switch, although other switch types known in the art may also be utilized.

Importantly, and as will be appreciated, the universal connection member comprising the annular plates 40, 46 may be shipped to manufacturers of various containers so that these plates 40, 46 can be integrated with such containers. Once such containers are outfitted with these platers, they can be used in conjunction with the UV sanitizing light module 10. Stated differently, the UV sanitizing light module can be used with any container which has adopted/integrated the universal plates 40, 46.

Further to the above, the module 10 may further include control electronics (e.g., a microprocessor or other control unit) and other hardware necessary for device operation. In an embodiment, these control electronics and hardware are configured to automatically provide power from the battery 20 to the light emitting elements 24 when the module 10 is connected to a container. In an embodiment, the control unit/microprocessor is configured to maintain the light emitting elements 24 in an energized state for a predetermined period of time, e.g., 3 minutes. Alternatively, the module 10 may have a user-activated switch (not shown) that can be manually activated and deactivated to actuate the light emitting elements 24. This switch may be the same or different from the switch that is activated upon engagement of the module 10 with a container. Still further, the switch and control unit may be configured such that when the switch is activated, the light emitting elements 23 are turned on for a predetermined time (such that to re-set after timeout you must unlock the module 10 and activate the manual switch again).

Referring now to FIGS. 5-32, various container systems utilizing the UV sanitizing light module 10 of the present invention are illustrated. In each of these embodiments, the module 10 may be modified to include an additional outer housing of the shape and configuration shown, or the housing 12 of the light module 10, itself, may take the shape and configuration illustrated (but have the same internal components as disclosed above).

With particular references to FIGS. 5-9, a UV sanitizing container system 100 according to an embodiment of the present invention is illustrated. The UV sanitizing container system 100 includes a container body 110 having an open interior space 112 for receiving item(s) to be sanitized, and a top opening 114 providing access to the open interior space 112 and outfitted with a connection member 116 (which may be, for example, an annular plate 116 with keyhole slots 118, as described above, although other connection means may also be utilized without departing from the broader aspects of the invention). As shown therein, the container body 110 may be generally cone or prism shaped (wherein the bottom has a larger cross-sectional area than the top), which allows UV light emitted from the module 10 to spread gradually to wide target area. In an embodiment, the container body 110 may be formed from a flexible fabric material. As shown therein, the UV sanitizing light module 10 may be removably connected to the top of the container body 110 via connection member (which may be, for example, a pair of lugs 120 that are received in the corresponding keyhole slots 118 in the annular plate 116 attached to the container body 110. As noted, above, the UV light sanitizing module 10 is substantially identical to that disclosed above, save for the outer housing having a different shape (in this case, cylindrical).

As also shown in FIGS. 5-9, in an embodiment, the module 10 may also include a slightly different connection member 116 than that disclosed above in connection with FIGS. 1-4, and may include an accent ring 122. Still further, the module 10 may include a charging port 124 (e.g., a USB charging port) electrically connected to the battery for recharging the battery when connected to a power source, and a LED indicator light 126 that is actuated when the UV light emitting elements 24 are activated to provide a visual indication to a user that the UV light emitting element are energized and sanitization is in progress. The indicator light 126 may be timed and/or controlled to the sanitization process such that the light is automatically turned off by the controller when sanitization is complete and the UV light emitting elements 24 are deactivated.

Figures 8, 9:
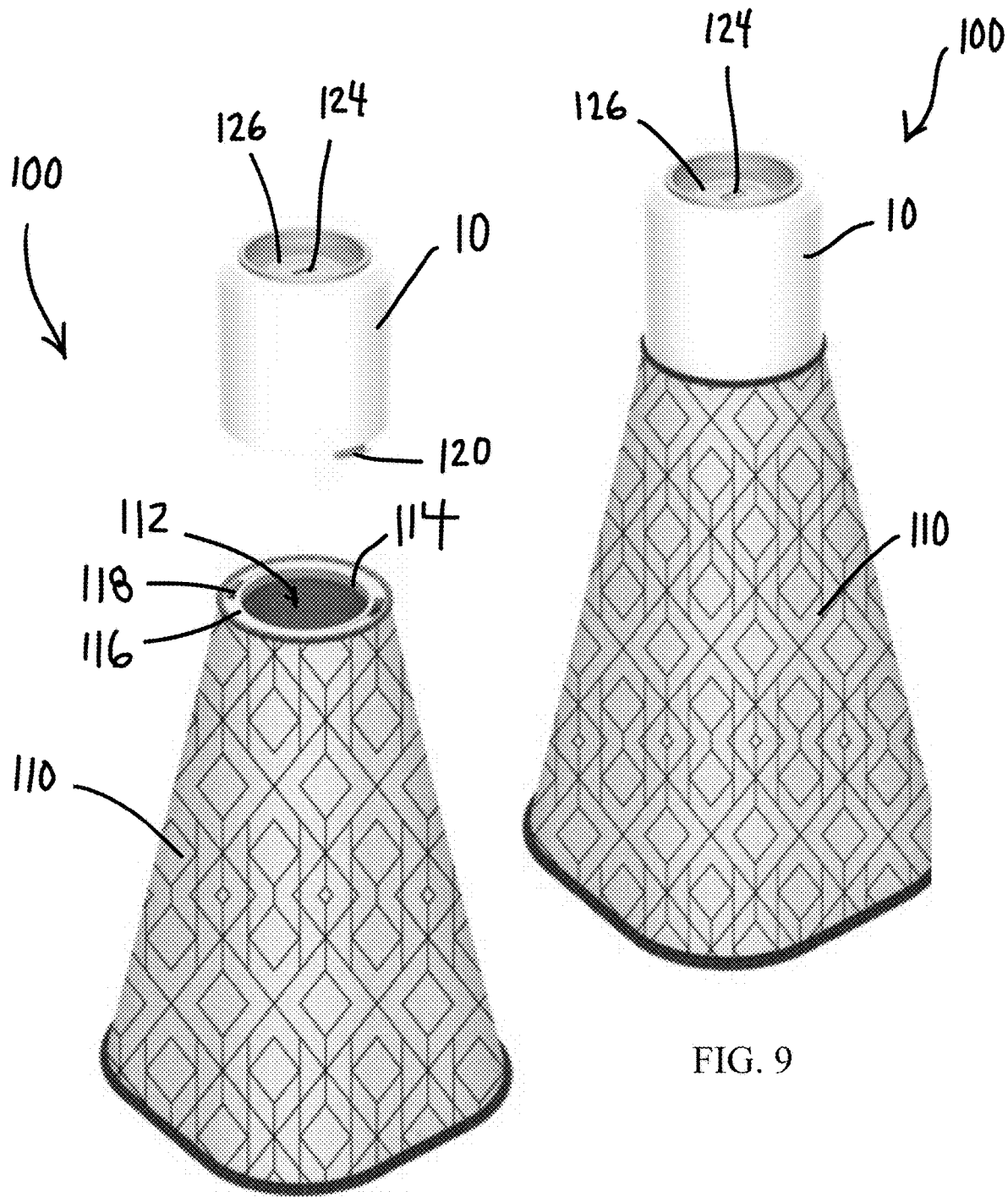
FIG. 8 is a perspective view of the container system of FIG. 5, showing the UV sanitizing light module decoupled from the container.
FIG. 9 is a perspective view of the container system of FIG. 5, showing the UV sanitizing light module coupled to the container.
Figure 10:
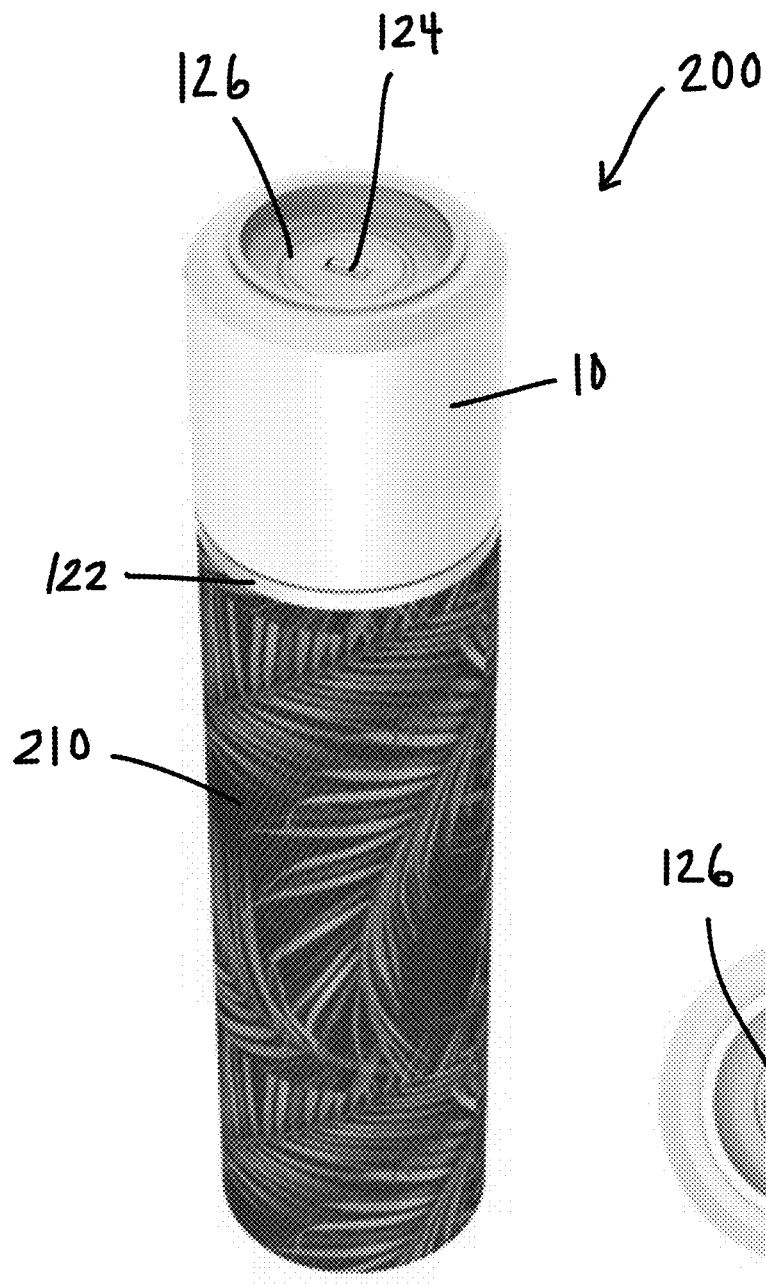
FIG. 10 is a perspective view of a container system having a UV sanitizing light module, according to another embodiment of the present invention.
Figure 11:
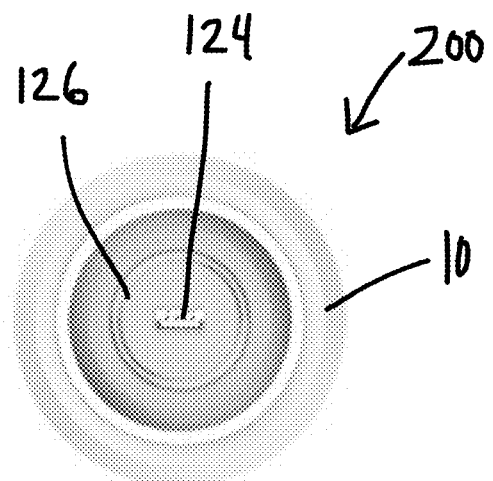
FIG. 11 is a top plan view of the container system of FIG. 10.
Figure 12:
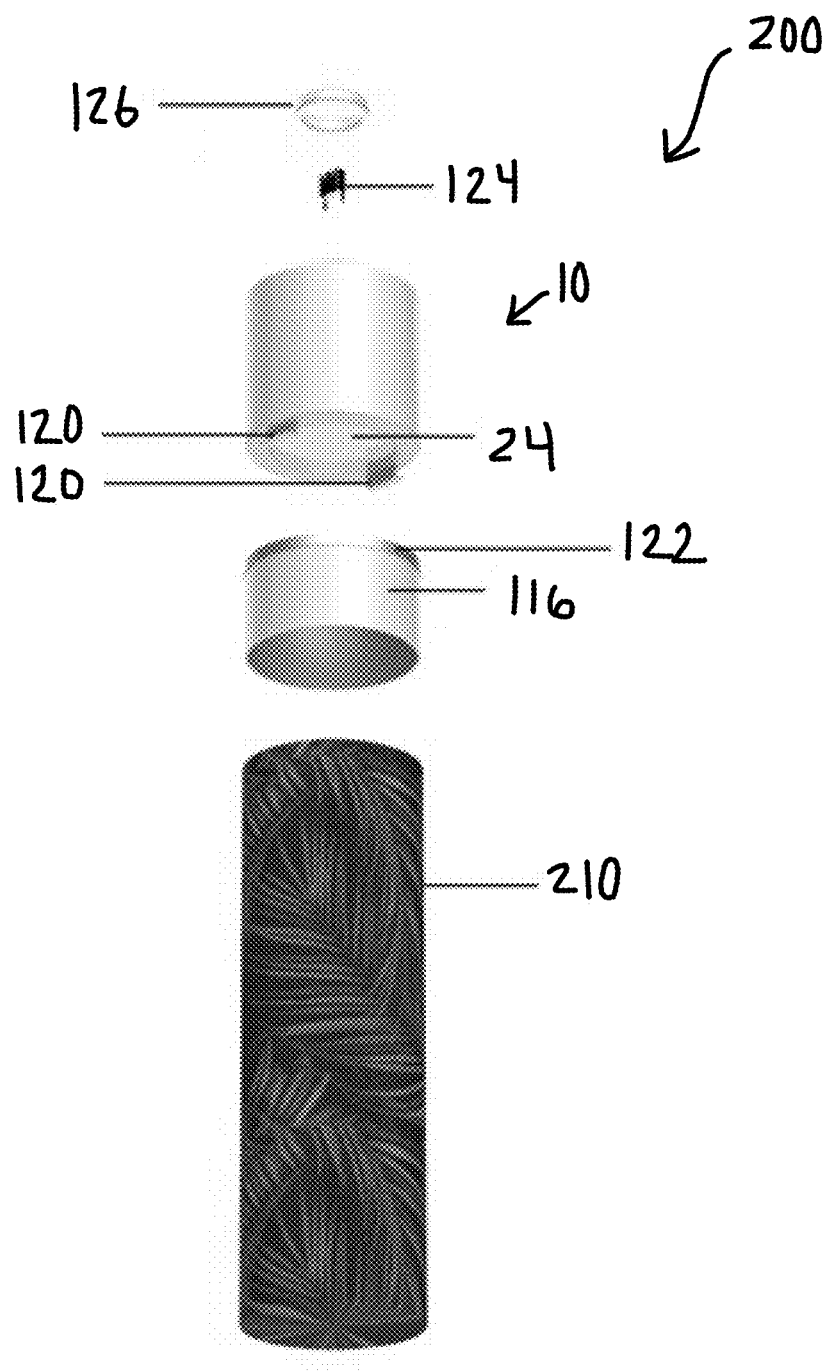
FIG. 12 is an exploded, perspective view of the container system of FIG. 10.
Figure 13:
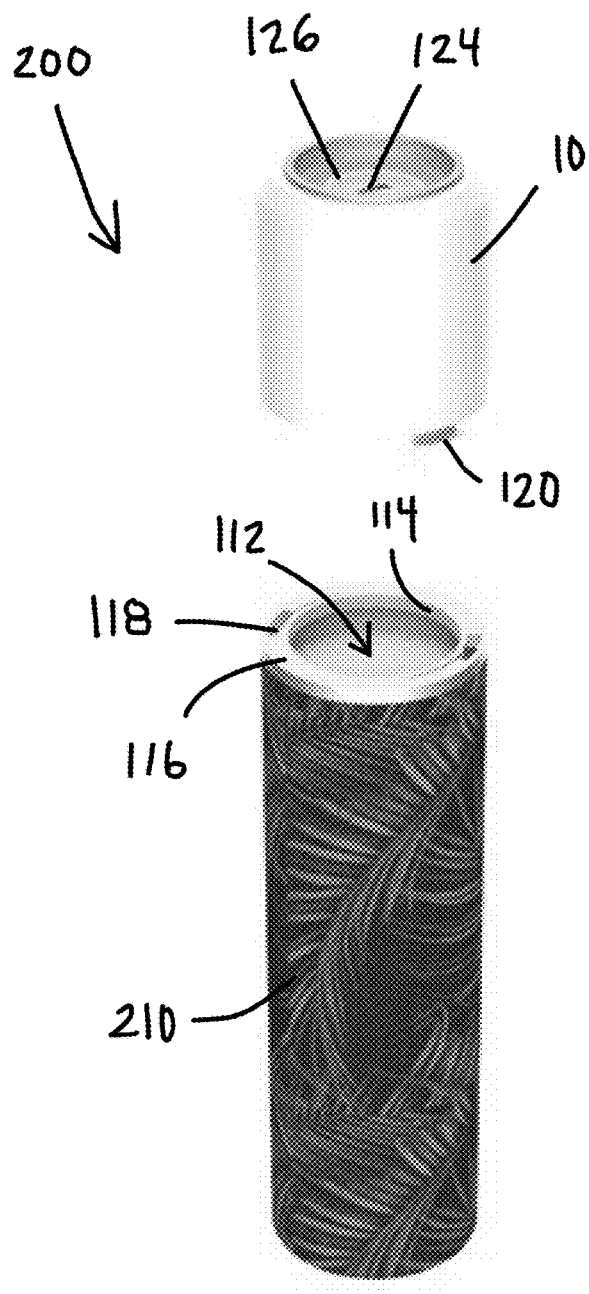
FIG. 13 is a perspective view of the container system of FIG. 10, showing the UV sanitizing light module decoupled from the container.
Figure 14:
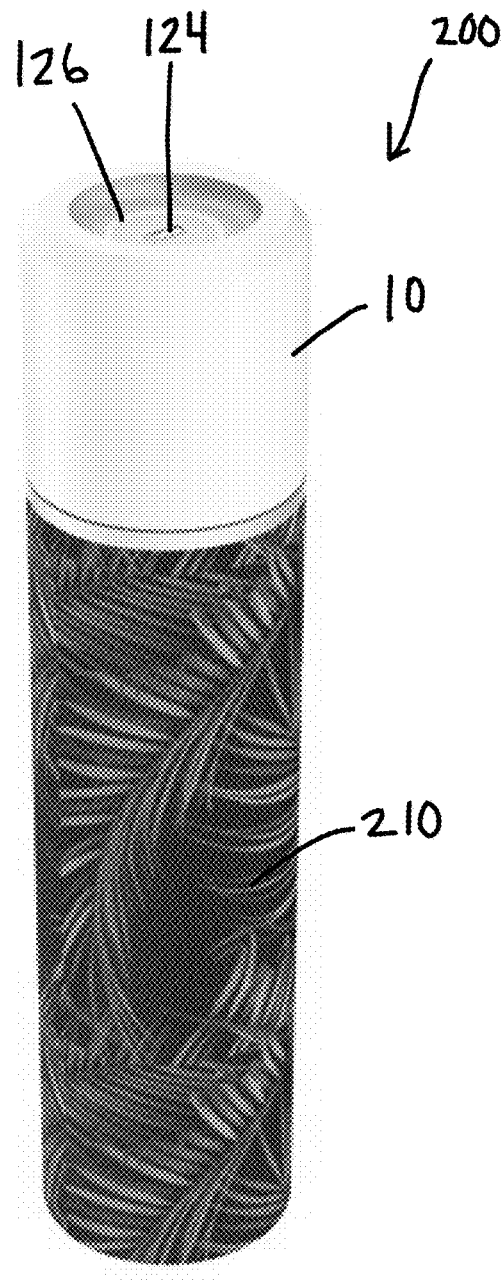
FIG. 14 is a perspective view of the container system of FIG. 10, showing the UV sanitizing light module coupled to the container.
Figures 15, 16:
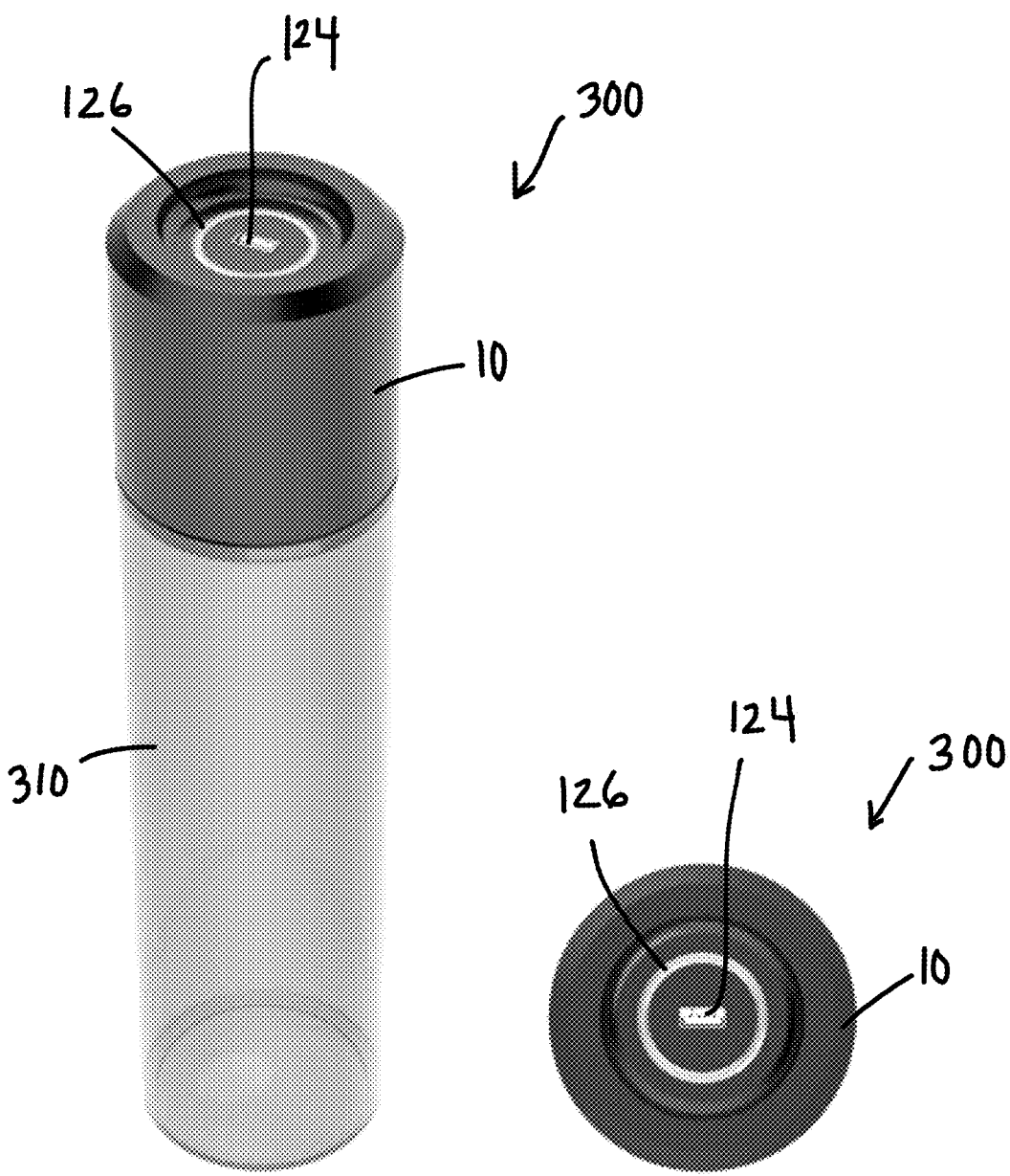
FIG. 15 is a perspective view of a container system having a UV sanitizing light module, according to another embodiment of the present invention.
FIG. 16 is a top plan view of the container system of FIG. 15.
Figure 17:
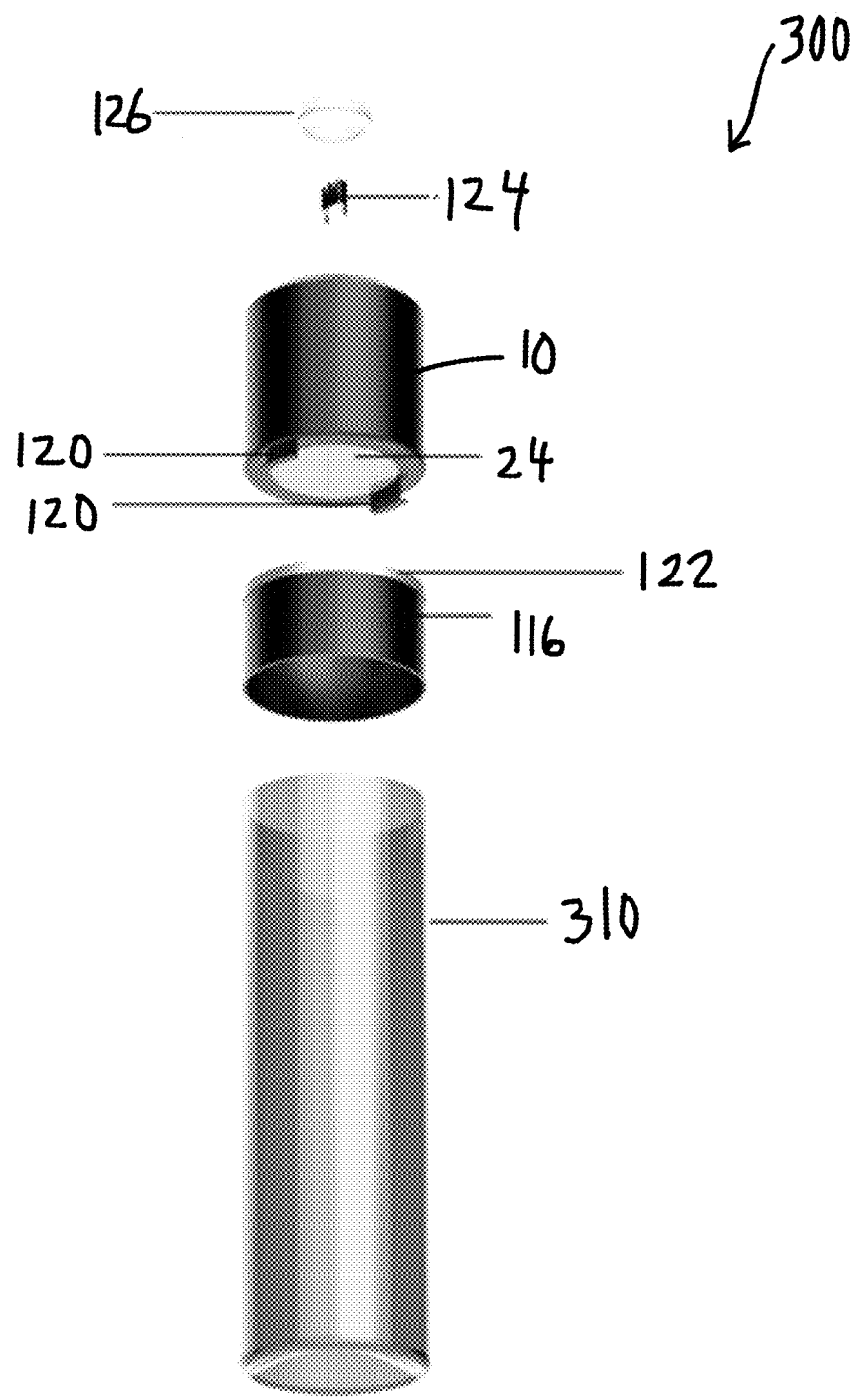
FIG. 17 is an exploded, perspective view of the container system of FIG. 15.
Figure 18:
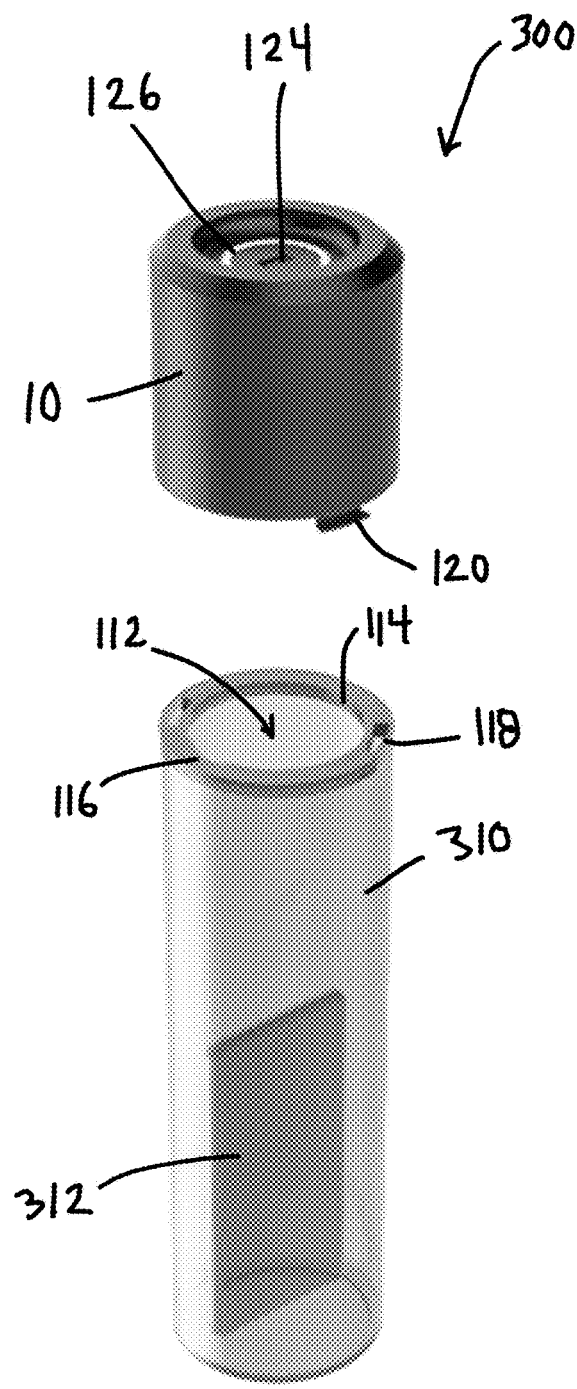
FIG. 18 is a perspective view of the container system of FIG. 10, showing the UV sanitizing light module decoupled from the container.
Figure 19:
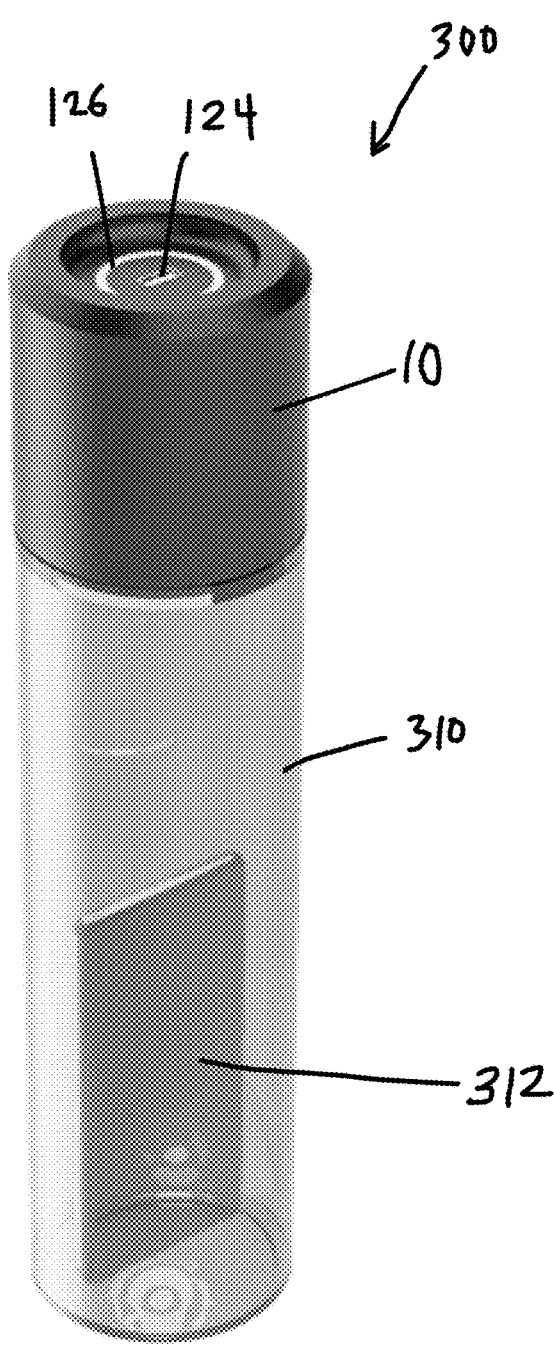
FIG. 19 is a perspective view of the container system of FIG. 15, showing the UV sanitizing light module coupled to the container.

With specific references to FIGS. 8 and 9, in operation, the container body 100 is opened by removing the UV sanitizing light module 10 from the top opening 114. Items to be sanitized such as a mobile phone, keys, masks and/or other items are placed in the interior space 112 through the top opening 114. The UV sanitizing light module 10 is then placed atop the container body 110 and connected thereto using the cooperating connecting members on the bottom of the module 10 and the top of the container body 110. As described above, the UV light emitting elements 24 are then either automatically activated (upon automatic detection of the module in locked position atop the container body 110), or via a manual switch (not shown). The UV light emitting element 24 emit light (preferably light in the UV-C range), which exits the module 10 through the slots in the grill 28. The UV light enters the container body 110 through the top opening 114 and illuminates the interior space 112, and the items contained therein, sanitizing such items. Upon completion of the sanitization process, the UV light emitting elements 24 are deactivated and the module 10 is decoupled from the container body 110 so that the sanitized and/or disinfected items may be removed.

Referring now to FIGS. 10-14, a UV sanitizing container system 200 according to another embodiment of the present invention is illustrated. The UV sanitizing container system 200 is generally the same in configuration and operation as container system 100, where like reference numerals designate like parts. Rather than having a cone-shaped container body, however, container system 200 has a generally cylindrical container body 210 that may likewise be made of fabric.

Turning to FIGS. 15-19, a UV sanitizing container system 300 according to another embodiment of the present invention is illustrated. The UV sanitizing container system 300 is generally the same in configuration and operation as container system 100, where like reference numerals designate like parts. Rather than having a cone-shaped container body, however, container system 300 has a generally cylindrical container body 310. The container body 310 is preferably formed plastic or other rigid material, and is preferably transparent or translucent, allowing a user to see the items, such as mobile phone 312 placed inside the interior space 112. Importantly, the transparent material of the body 310 enables a user to see when the glow of the UV light emitting elements 24 emitting by the UV sanitizing light module 10 through the sides and bottom of the container body 310, when the UV light emitting elements 24 are activated or energized, but blocks/absorbs radiation from reaching a user.

Figure 20:
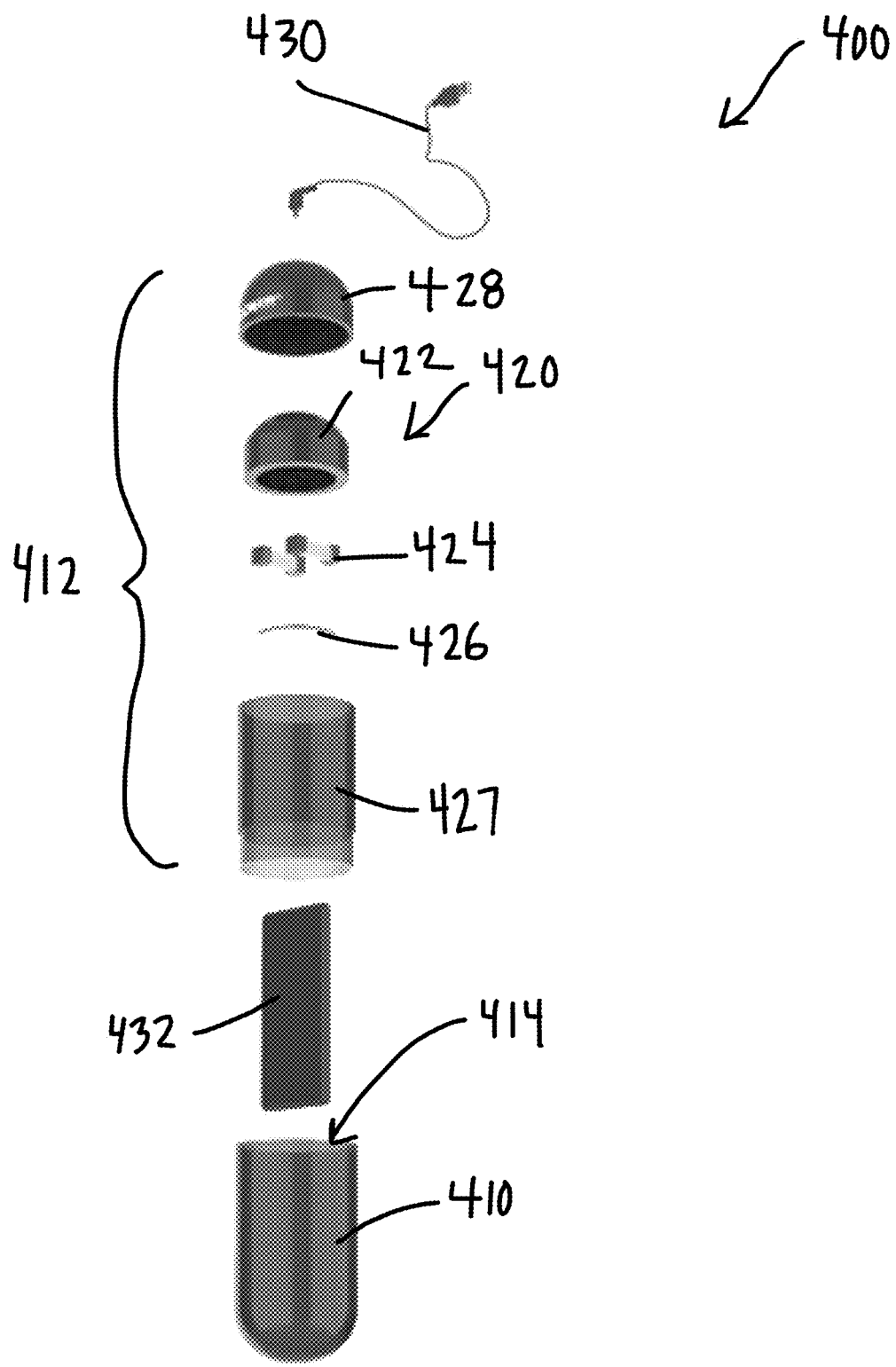
FIG. 20 is an exploded, perspective view of a container system having a UV sanitizing light module, according to another embodiment of the present invention.
Figure 21:
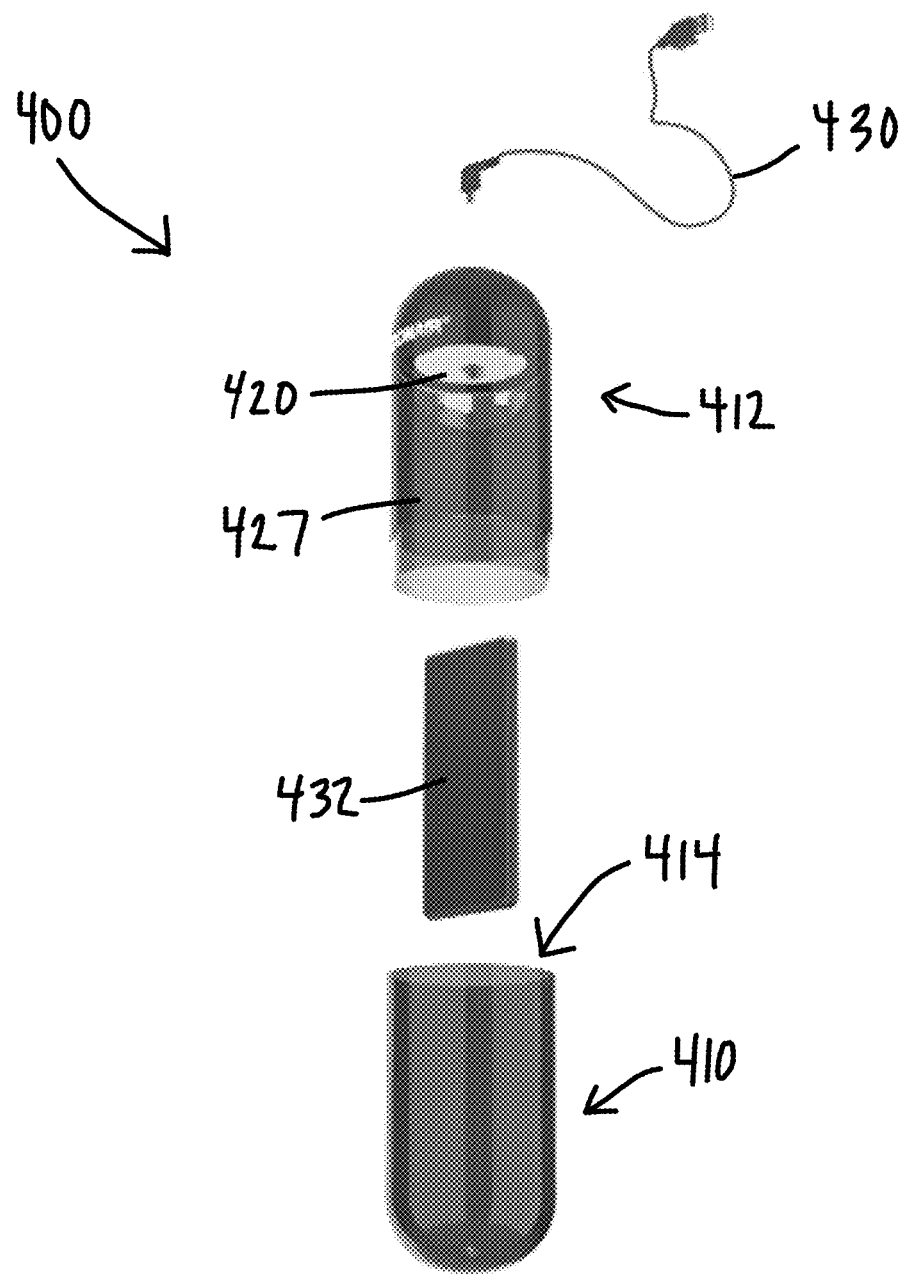
FIG. 21 is a perspective view of the container system of FIG. 20, showing the container in an open position.
Figure 22:
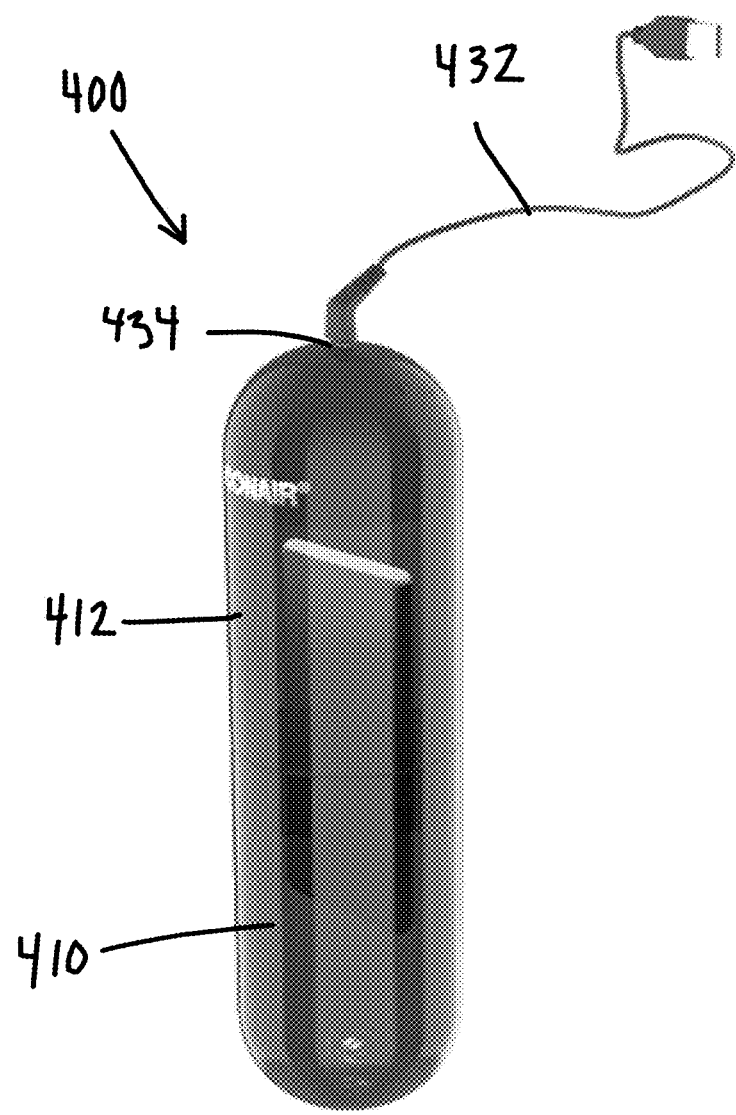
FIG. 22 is a perspective view of the container system of FIG. 20, showing the container in a closed, sanitizing position.

FIGS. 20-22 illustrate a UV sanitizing container system 400 according to yet another embodiment of the present invention. The UV sanitizing container system 400 includes a lower housing portion 410 and an upper housing portion 412 configured for removable connection to the lower housing portion 410 such that, when interconnected, the container system 400 is generally capsule shaped and defines therein an open interior space 414. As best shown in FIGS. 20 and 21, the UV sanitizing container system 400 also includes a UV sanitizing light module 420 that is generally similar in configuration and function to UV sanitizing light module 10, described above. As shown therein, the module 420 includes a housing 422 (similar to housing 12) that contains at least one UV light emitting element 424 (e.g., UV light emitting diodes), a battery and/or other control and electrical components necessary for powering of the UV light emitting elements 424 and for control of the sanitization process, as described above. Rather than having a grill, however, the module 420 may include a transparent lens 426 that is received on the open end of the housing 422 and which allows UV light emitted by the UV light emitting elements to enter the lower housing 410. As shown therein, the UV sanitizing light module 420 forms part of the upper housing 412, which also includes a generally cylindrical portion 427 and an end cap 428. The upper housing may also include a port 434 for connection of a power and/or charging cable 430 (e.g., a USB cord) for recharging the battery and/or powering the UV light emitting elements 424).

In an embodiment, the lower housing portion 412 and the cylindrical portion 427 of the upper housing portion 412 may be transparent or translucent, allowing a user to see the items, such as mobile phone 432 placed inside the interior space 414. Importantly, the transparent material enables a user to see when the glow of the UV light emitting elements 424 emitting by the UV sanitizing light module 420 through the sides and bottom of the container 400 when the UV light emitting elements 424 are activated or energized, but blocks/absorbs radiation from reaching a user.

In use, the upper and lower housing portions 410, 412 may be decoupled, providing access to the interior space 414. Items to be sanitized are then placed in the lower housing portion 410, and the upper housing portion 412 is connected to the lower housing portion 410 to enclose the items. Sanitizing via UVC radiation emitted by the light emitting elements 424 is then carried out in any of the manners described above (e.g., via manual or automatic operation). Upon completion of sanitization, the housing portions 401, 412 are decoupled and the items may be retrieved.

Figure 23:
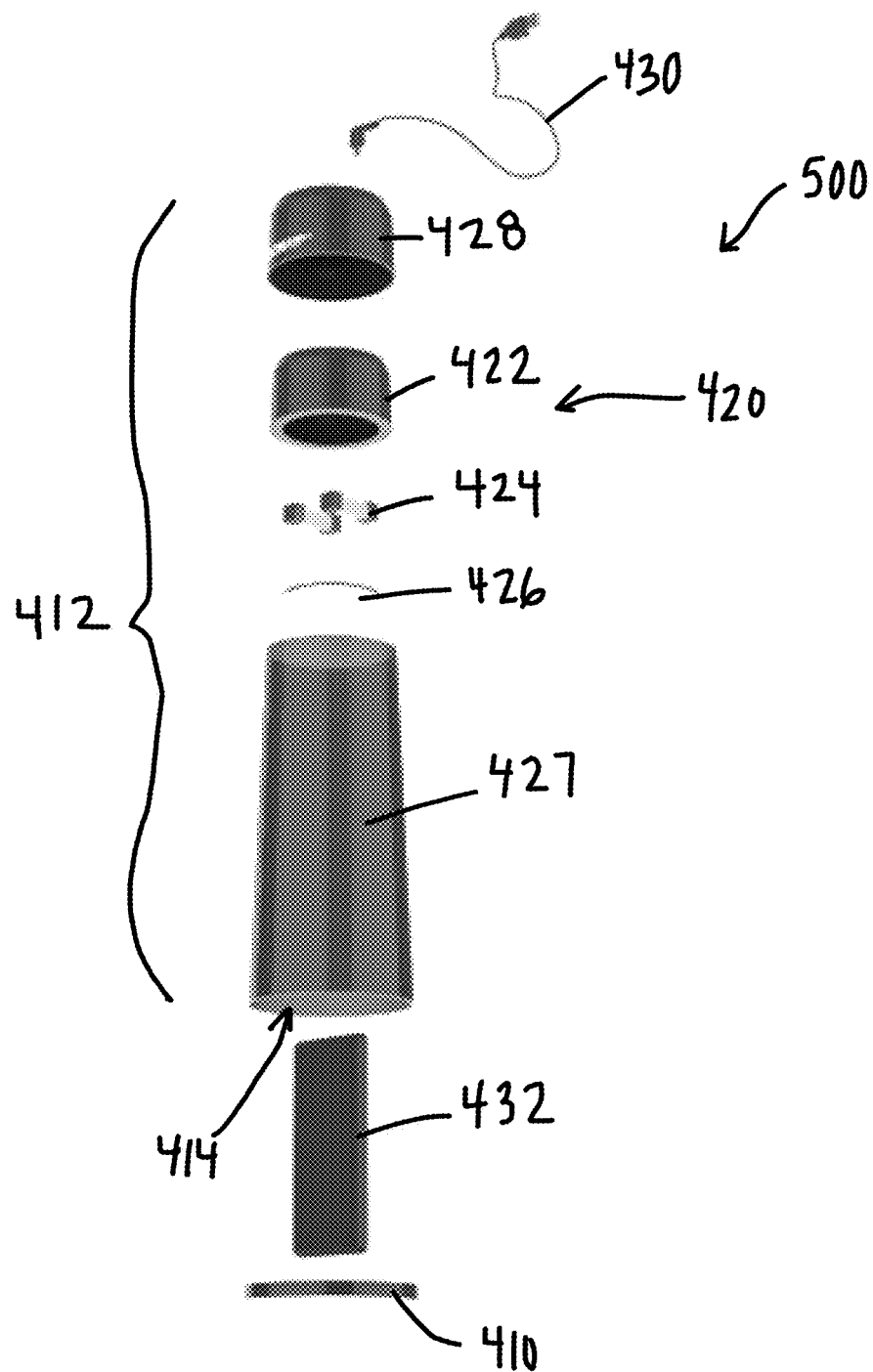
FIG. 23 is an exploded, perspective view of a container system having a UV sanitizing light module, according to another embodiment of the present invention.
Figure 24:
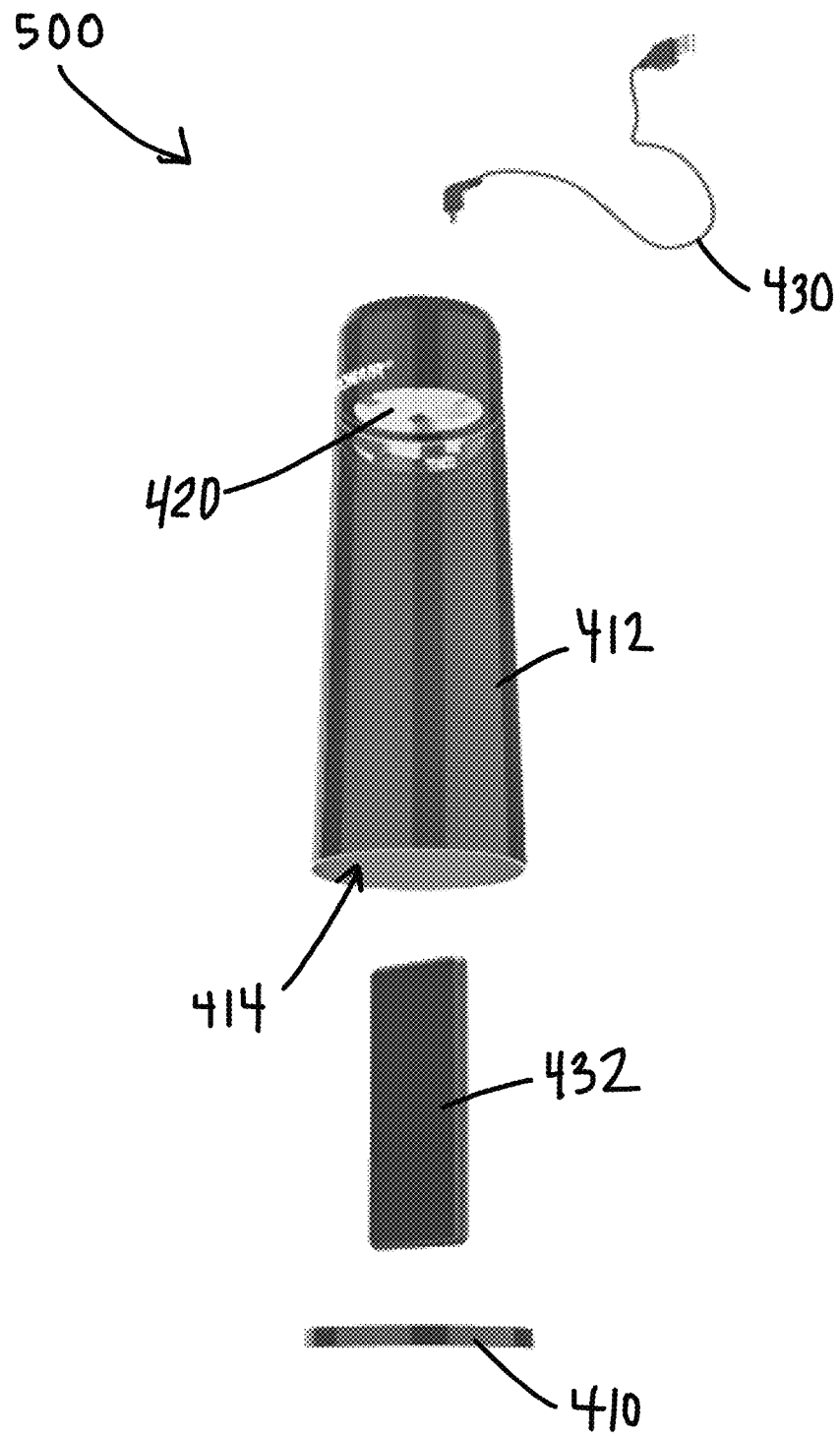
FIG. 24 is a perspective view of the container system of FIG. 23, showing the container in an open position.
Figure 25:
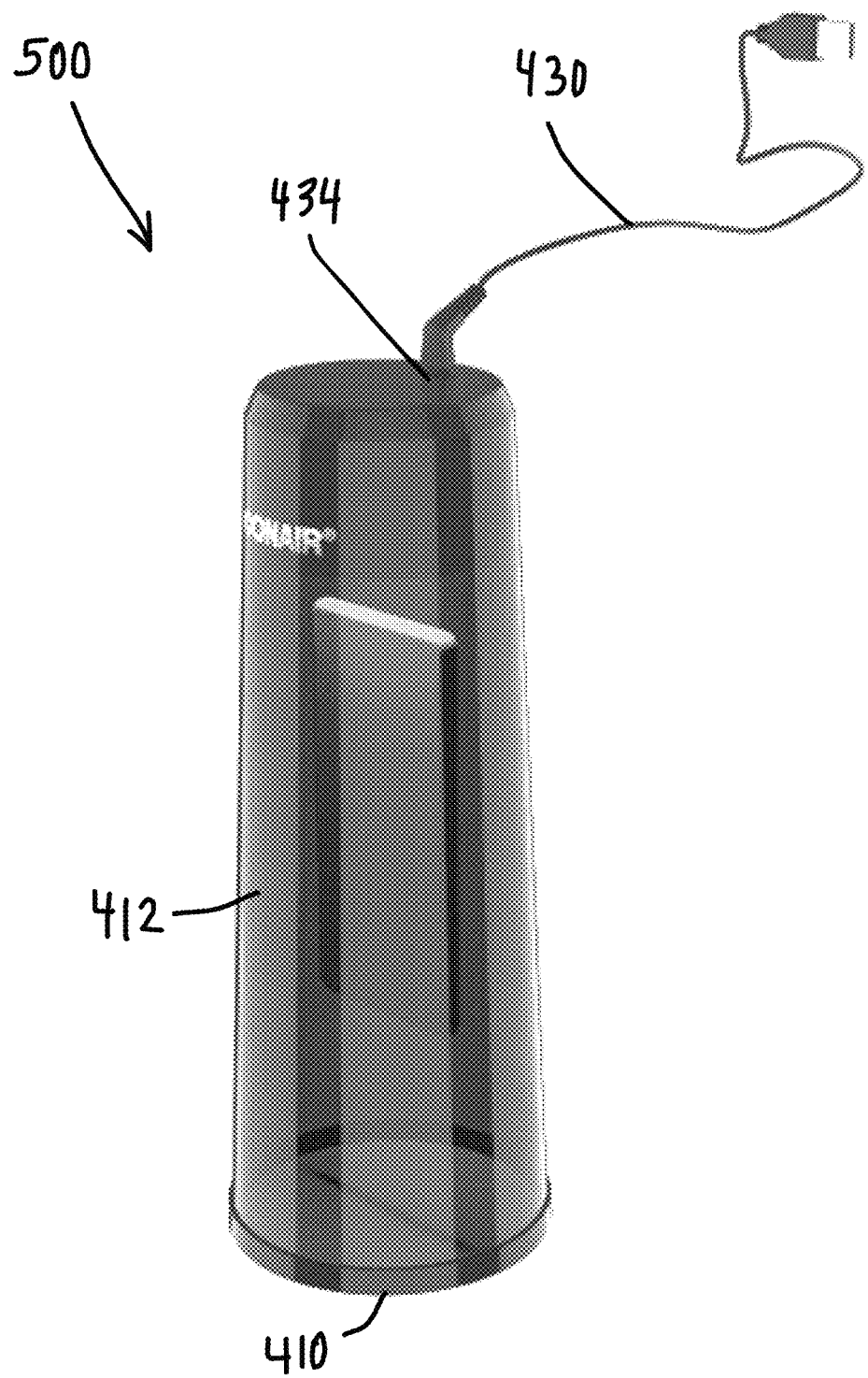
FIG. 25 is a perspective view of the container system of FIG. 23, showing the container in a closed, sanitizing position.

Turning to FIGS. 23-25, a UV sanitizing container system 500 according to another embodiment of the present invention is illustrated. The UV sanitizing container system 500 is generally the same in configuration and operation as container system 400, where like reference numerals designate like parts. Rather than being generally capsule shaped, however, the container 500 is generally cone shaped. In addition, the upper housing portion 427 forms a substantial entirety of the container 500, while lower housing portion 410 is configured as an end cap/that is received by the upper housing portion 427 to enclose the interior space 414. In an embodiment, the end cap may be a snap on, flexible lid. Like the container 400 disclosed above, the upper housing portion 427 of the upper housing 412 of the container system 500 may be transparent or translucent.

Figure 26:
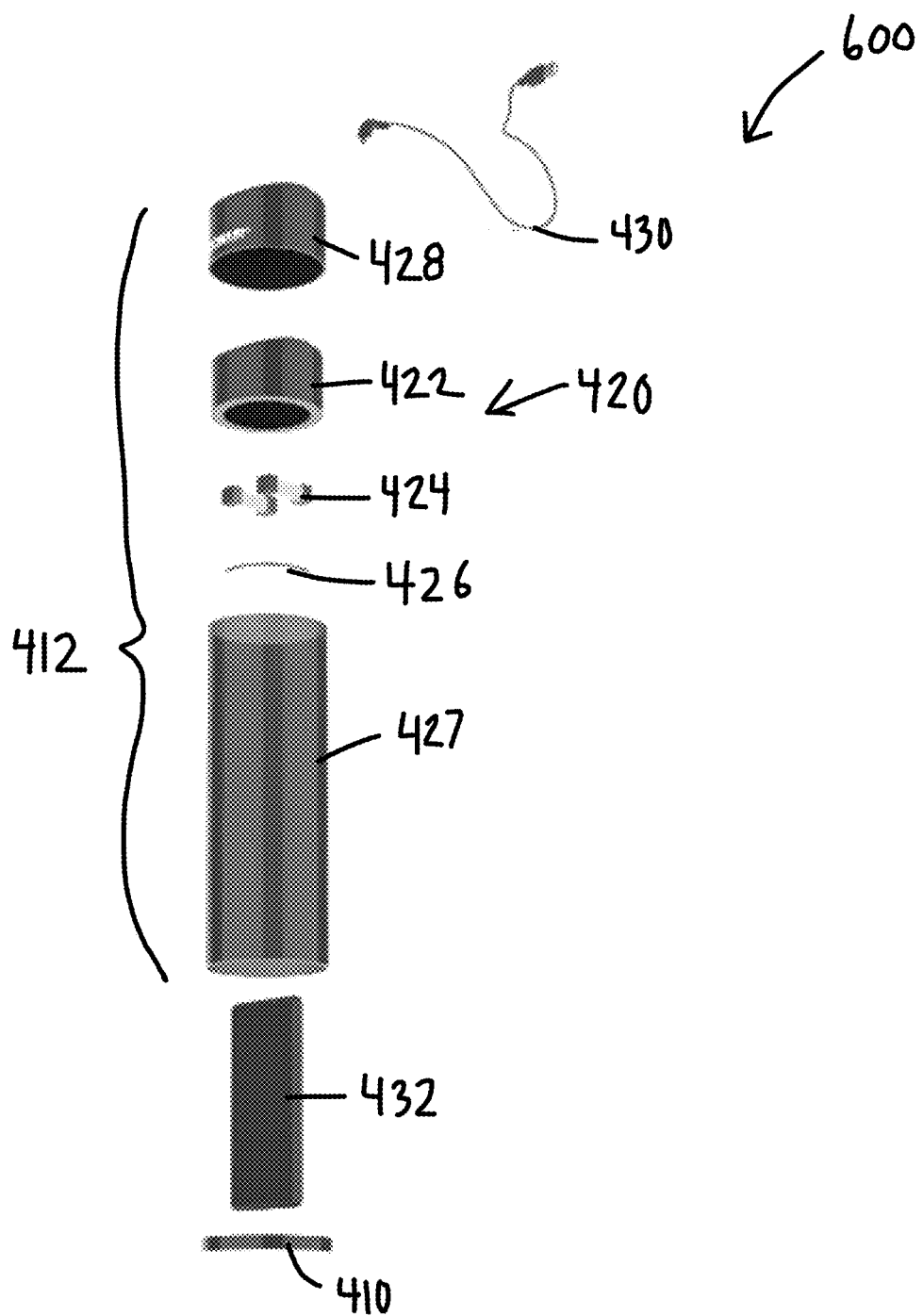
FIG. 26 is an exploded, perspective view of a container system having a UV sanitizing light module, according to another embodiment of the present invention.
Figure 27:
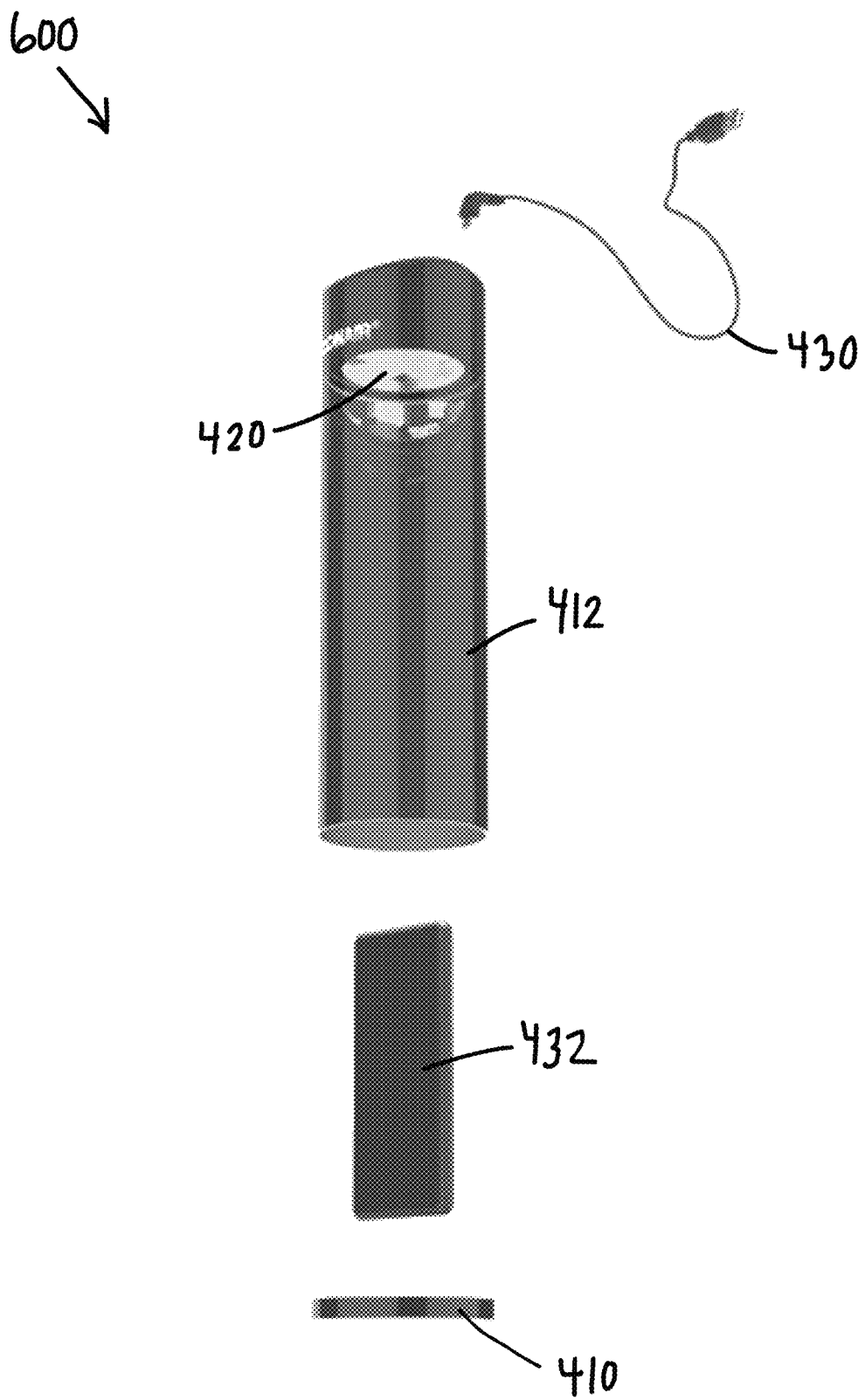
FIG. 27 is a perspective view of the container system of FIG. 26, showing the container in an open position.
Figure 28:
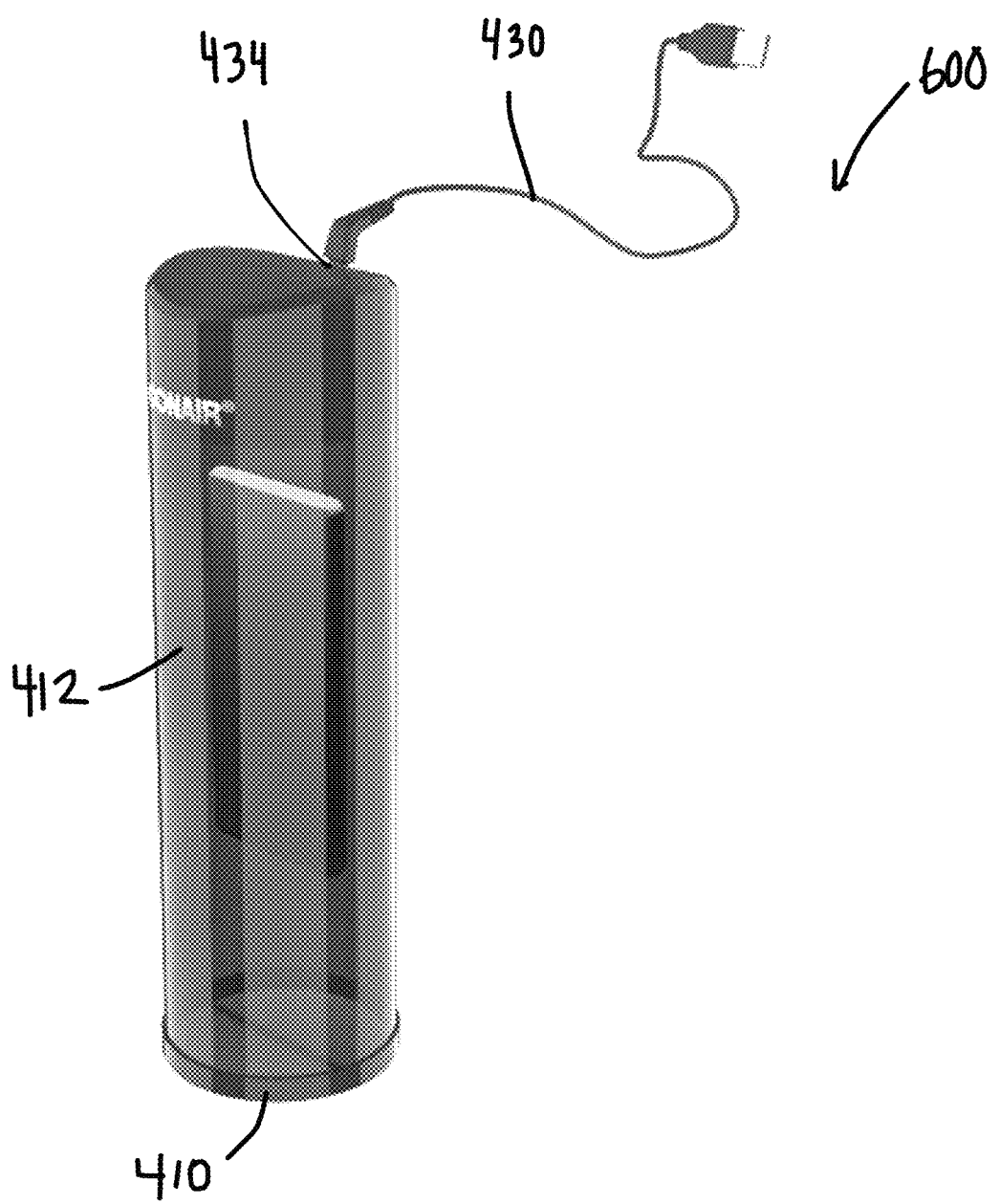
FIG. 28 is a perspective view of the container system of FIG. 26, showing the container in a closed, sanitizing position.
Figure 29:
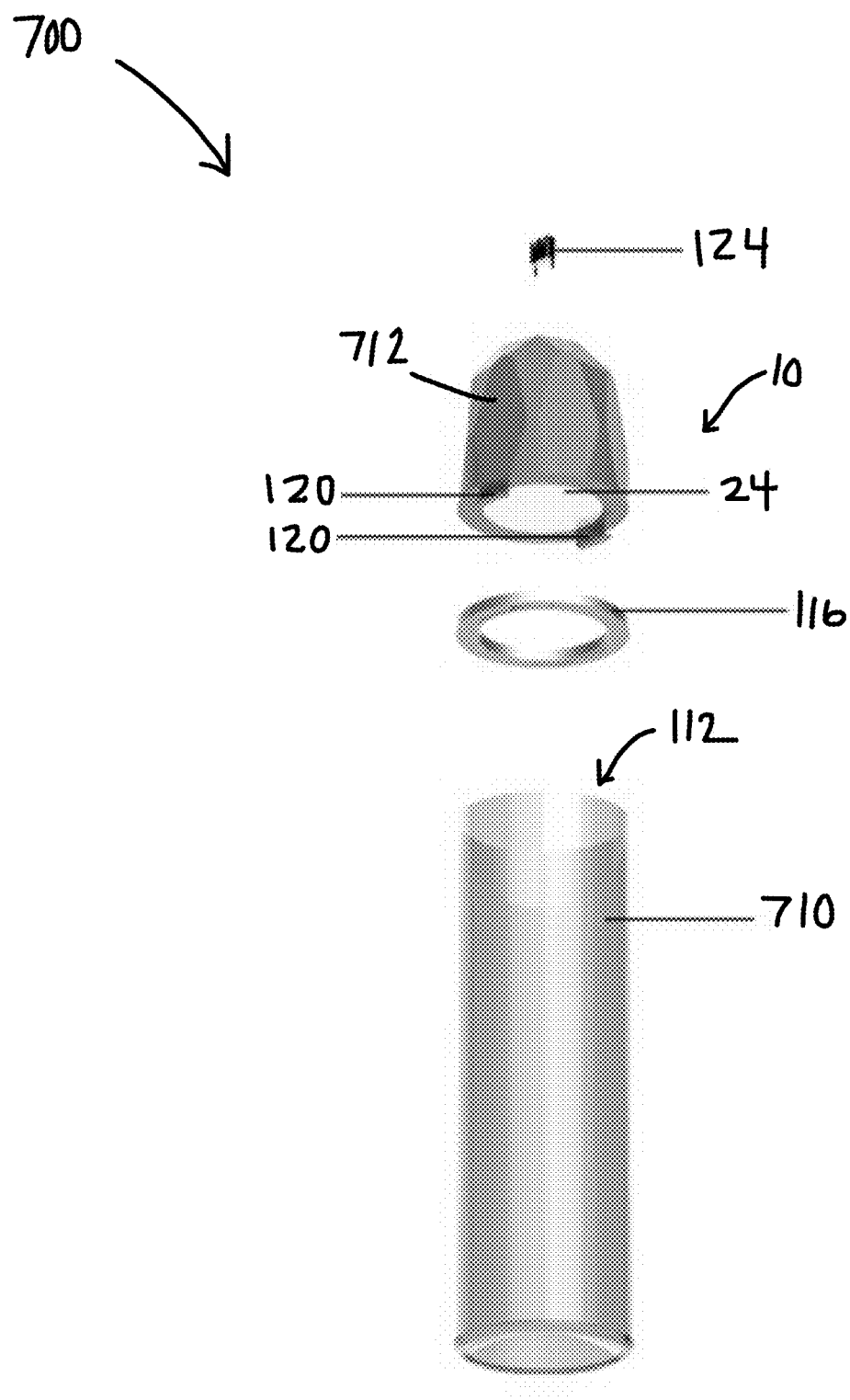
FIG. 29 is an exploded, perspective view of a container system having a UV sanitizing light module, according to another embodiment of the present invention.
Figure 30:
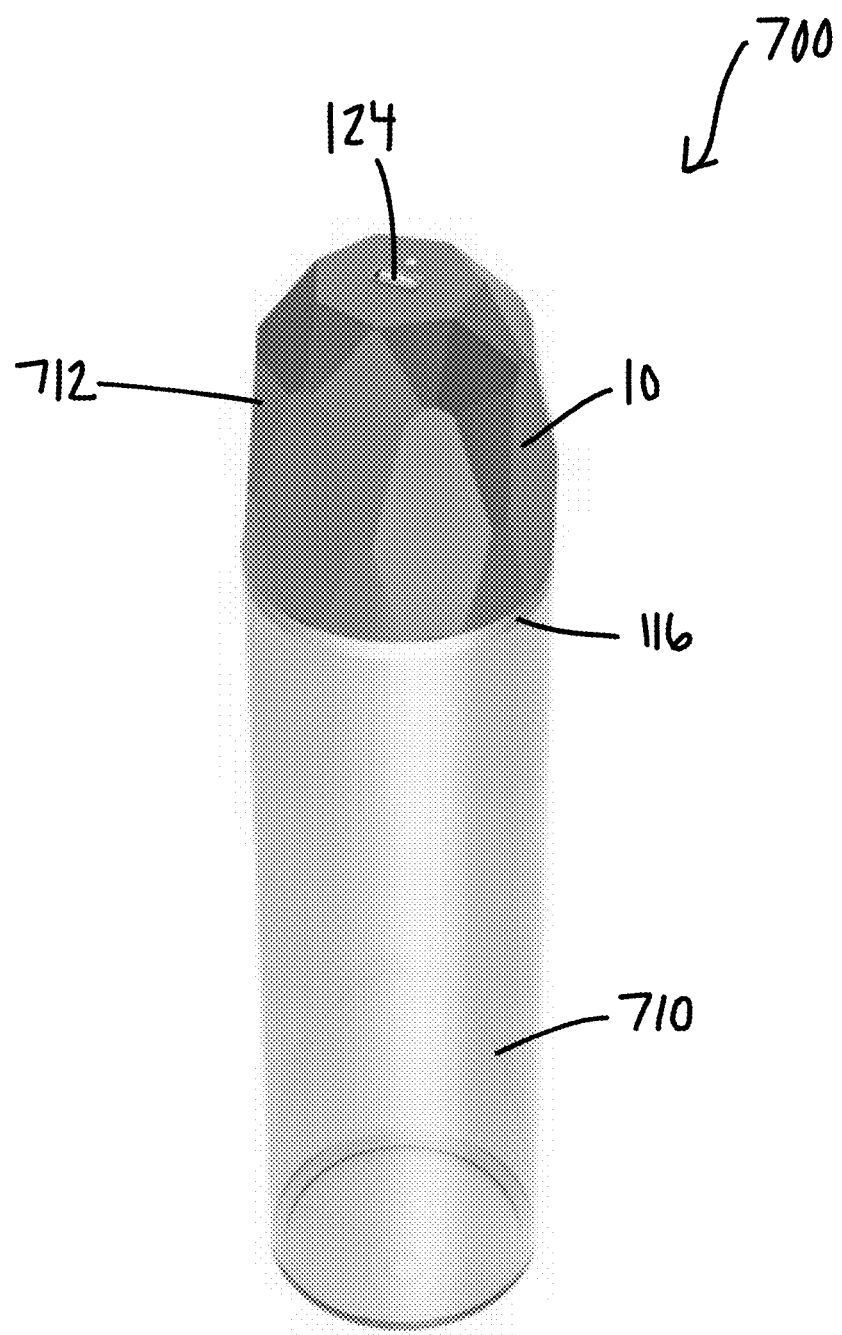
FIG. 30 is a perspective view of the container system of FIG. 29, showing the container in a closed, sanitizing position.
Figures 31, 32:
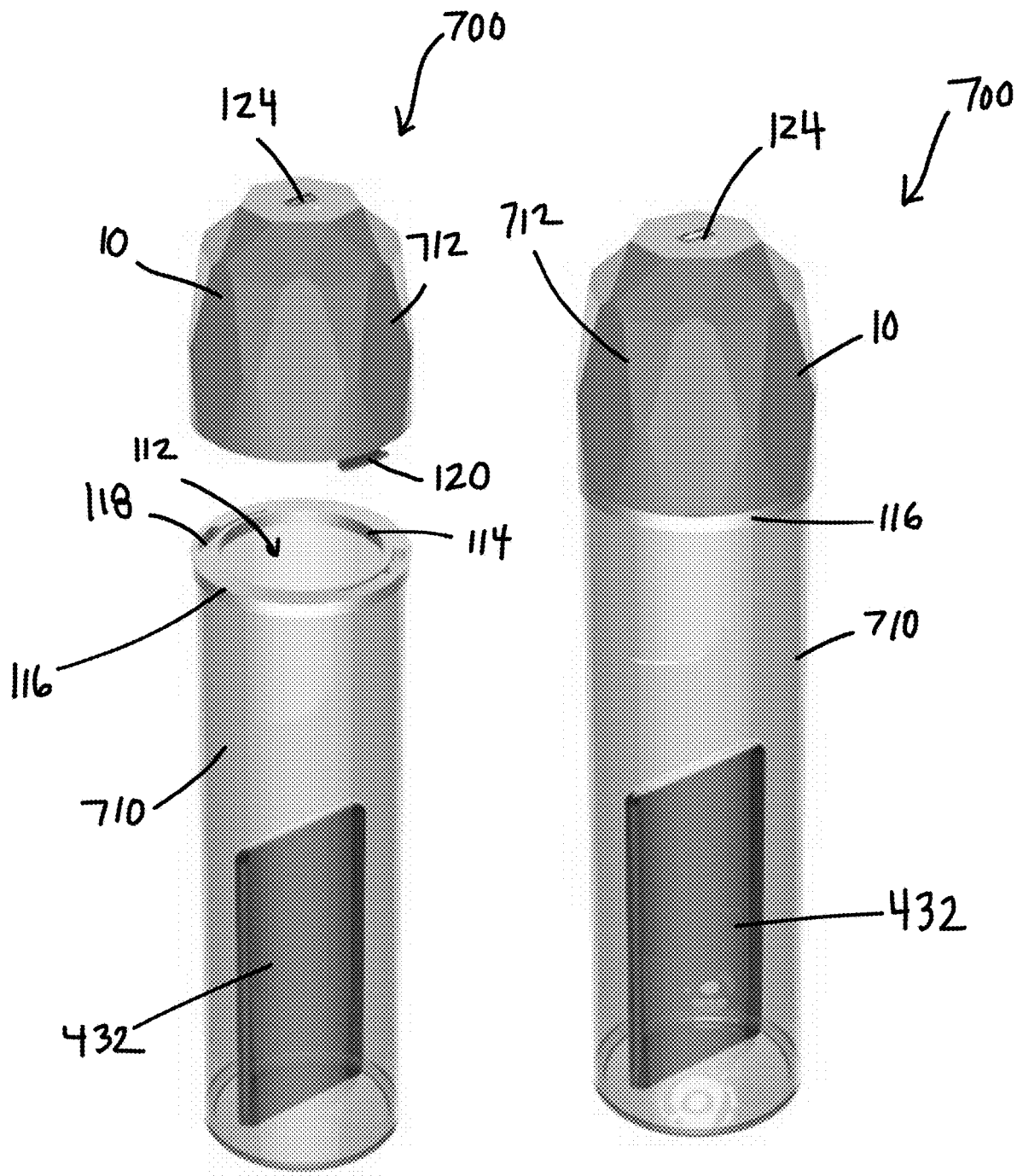
FIG. 31 is a perspective view of the container system of FIG. 29, showing the container in an open position.
FIG. 32 is a perspective view of the container system of FIG. 29, showing the container in a closed, sanitizing position.

With reference to FIGS. 26-28, a UV sanitizing container system 600 according to another embodiment of the present invention is illustrated. The UV sanitizing container system 600 is generally the same in configuration and operation as container system 500, where like reference numerals designate like parts. Rather than being generally cone-shaped, however, container 600 is generally cylindrical in shape.

Turning to FIGS. 29-32, a UV sanitizing container system 700 according to another embodiment of the present invention is illustrated. The UV sanitizing container system 700 is generally the same in configuration and operation as container system 200, where like reference numerals designate like parts. Rather than having a fabric container body/housing, however, the container body 710 is formed from a translucent or transparent material such as plastic. In addition, the outer housing 712 of the UV sanitizing light module 10 is multi-faceted, which provides for better ergonomics and gripping when attaching and detaching the module 10 to the container body 710.

In the embodiments disclosed herein, it is contemplated that the size and configuration of the container may be selected so that certain objects such as, for example, a mobile phone can stand up and not fall flat, which would then prevent UV light from reaching the entire bottom side of phone that is flat on floor. Moreover, in the embodiments described above, particularly the ones that do not utilize transparent containers, one or more of the interior surface of the containers may be formed or include a reflective material. This reflective material reflects the UV light towards the objects with the container, increasing sanitizing effectiveness.

In addition to the above, it is contemplated that the UV sanitizing light modules disclosed herein can be utilized with a variety of different containers configured to matingly engage the module. Accordingly, an end user may have a single UV sanitizing light module that can be used with a plurality of different containers. In this respect, a user can purchase a single UV sanitizing light module and multiple different containers and flexible bags that are compatible with the module, such that a single module can have multiple modes of use.

Figure 33:
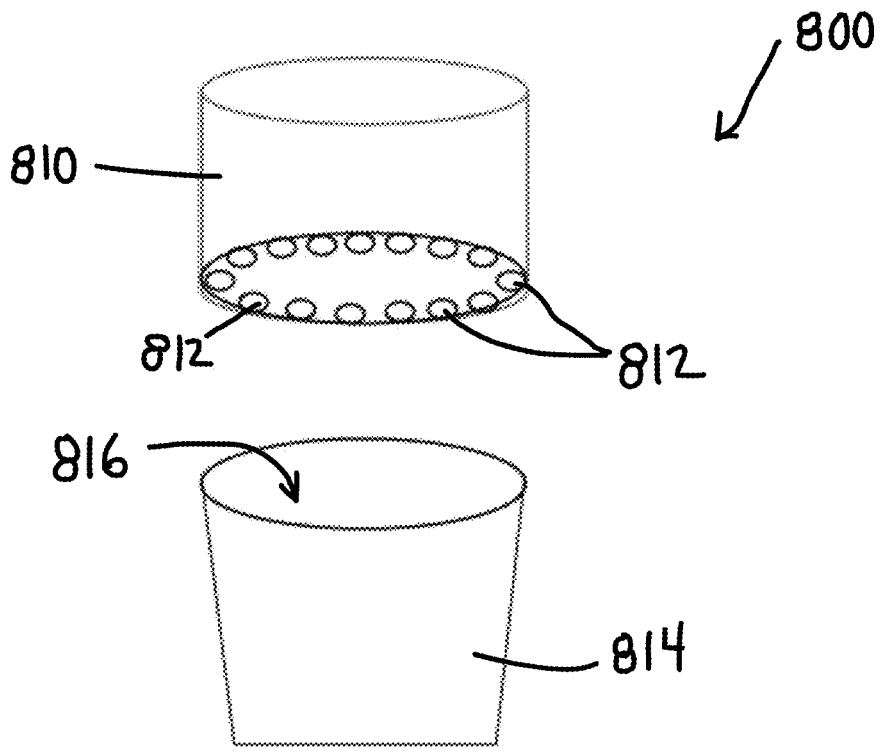
FIG. 33 is a perspective illustrating of a container system, according to another embodiment of the present invention, showing an open position.
Figure 34:
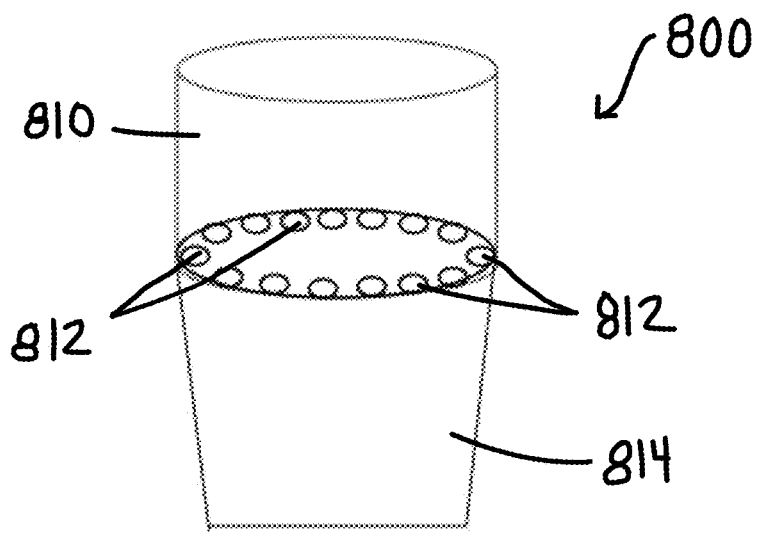
FIG. 34 is a perspective illustration of the container system of FIG. 33, showing a closed, sanitizing position.

Referring finally to FIGS. 33 and 34, a UV sanitizing container system 800 according to another embodiment of the present invention is illustrated. The UV sanitizing container system includes a UV sanitizing light module 810 having a plurality of UV light emitting elements 812. The UV sanitizing light module 810 may be generally similar in configuration and operation to the UV sanitizing light module 810 described above, and is configured for connection to a corresponding contain body or housing 814 having interior receiving space 816 using any means known in the art, such as a threaded connection, snap fit connection, bayonet connection, keyhole slot connection and/or magnetic connection, although other connection means known in the art may also be utilized without departing from the broader aspects of the present invention. As disclosed above, the UV sanitizing light module 810 is configured to emit UV light, and preferably UVC light, into the housing 814 for sanitizing objects placed therein.

In an embodiment, the housing 814 is shaped, sized and dimensions so as to be received in typical cup holder in an automobile so that it is readily available for sanitizing high tough items such as keys, phones, credit cards, bills, coins and other items. In an embodiment, the housing 814 may be rigid or semi-rigid so as to hold its shape and be received by a standard cup holder. In an embodiment, various power sources for the UV sanitizing light module 810 are envisioned such as, for example, a battery or rechargeable battery. In an embodiment, power or recharging capability may be provided by a dedicated power cord. The power cord may be configured for connection to a lighter plug/outlet, regular outlet, USB port, etc.

As described above, the UV LEDs of the sanitizing module of any of the embodiments described herein sanitizes and disinfects any items placed in an associated container to which the sanitizing module is connected. In particular, the intensity/wavelength of the UV LEDs may selected to kill bacteria, mold, yeast, fungi, and certain viruses present on objects placed in the container. The UV sanitizing light modules and container systems of the present invention, therefore, function to disinfect a variety of small, high touch items. As will be appreciated therefore, use of the UV sanitizing light module and container systems of the present invention inhibit the spread of bacteria and viruses, such as COVID-19, via contact with high touch items, to a degree heretofore not possible with the convention means such as antibacterial solutions and wipes.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A sanitizing module, comprising:
a dome-shaped housing having an open end, the housing including a plurality of protrusions arranged in an annular configuration on an exterior surface of the housing distal from the open end, the plurality of protrusions enabling gripping of the housing by a palm of a hand of a user;
at least one ultraviolet light emitting element within the housing and being configured to emit ultraviolet light out of the housing through the open end; and
a grill connected to the open end of the housing, the grill defining a plurality of slots;
wherein the housing is configured for removable connection to an open upper end of a container having an interior receiving space such that connection of the housing to the container encloses the interior receiving space of the container;
wherein the slots in the grill are configured to allow the ultraviolet light to pass therethrough and into the interior receiving space of the container;
wherein the sanitizing module further includes a first connection member associated within the open end of the housing, the first connection member being configured to cooperate with a corresponding second connection member on the container, the first connection member and the second connection member forming a connection mechanism for removably connecting the housing to the container; and
wherein the connection mechanism is a bayonet connection; and
wherein a diameter of an annulus defined by the annular configuration of the plurality of protrusions is less than a diameter of the housing.

2. The sanitizing module of claim 1, wherein:
the at least one ultraviolet light emitting element is a plurality of ultraviolet light emitting elements.

3. The sanitizing module off claim 2, wherein:
the plurality of ultraviolet light emitting elements are ultraviolet light emitting diodes.

4. The sanitizing module of claim 3, wherein:
the ultraviolet light has a wavelength between about 100 nanometers to about 280 nanometers.

5. The sanitizing module of claim 1, further comprising:
a battery within the housing, the battery being electrically connected to the at least one ultraviolet light emitting element for powering the at least one ultraviolet light emitting element.

6. The sanitizing module of claim 1, further comprising:
a port in the housing, the port being configured for connection to a power source for at least one of powering the at least one ultraviolet light emitting element and/or recharging a battery within the housing.

7. The sanitizing module of claim 1, wherein:
the at least one light emitting element is a plurality of light emitting elements arranged in an annular configuration.

8. A sanitizing container system, comprising:
a sanitizing module having a housing and at least one ultraviolet light emitting element within the housing;
a container having an open end and an interior receiving space, the open end providing access to the interior receiving space;
wherein the container further includes a connection mechanism at the open end allowing for the removable connection of the sanitizing module to the container to enclose the interior receiving space;
wherein the at least one ultraviolet light emitting element is configured to emit ultraviolet light from the housing and into the interior receiving space of the container;
wherein the container has a tapered prism shape and has flat sidewalls such that a cross-sectional area of the container adjacent to the open end is smaller than a cross-sectional area at a bottom end opposite the open end; and
wherein the housing is dome-shaped and includes a plurality of protrusions arranged in an annular configuration on an exterior surface of the housing distal from the open end, the plurality of protrusions enabling gripping of the housing by a palm of a hand of a user.

9. The sanitizing container system of claim 8, wherein:
the at least one ultraviolet light emitting element is a plurality of ultraviolet light emitting elements; and wherein the plurality of ultraviolet light emitting elements are ultraviolet light emitting diodes configured to emit the ultraviolet light having a wavelength between about 100 nanometers to about 280 nanometers.

10. The sanitizing container system of claim 8, wherein:
the sanitizing module is configured to automatically activate the at least one ultraviolet light emitting element upon connection of the sanitizing module to the container.

11. The sanitizing container system of claim 8, wherein:
the container is shaped and dimensioned to be received in an automobile cup holder.

12. The sanitizing container system of claim 8, wherein:
the container is transparent or translucent.

13. The sanitizing container system of claim 8, wherein:
the container is formed from a fabric material.

14. The sanitizing container system of claim 8, further comprising:
wherein the connection mechanism is at least one of a magnetic coupling, a threaded connection, a snap fit connection, a bayonet connection and/or a keyhole slot connection.

15. A method of sanitizing an object, comprising the steps of:
providing a sanitizing module having a housing and at least one ultraviolet light emitting element within the housing;
providing a first container having an open end and an interior receiving space, the open end providing access to the interior receiving space; and
connecting the sanitizing module to the open end of the first container to enclose the interior receiving space, whereby the at least one ultraviolet light emitting element emits ultraviolet light from the housing and into the interior receiving space of the first container when the sanitizing module is connected to the first container;
providing a second container having an open end and an interior receiving space, the open end providing access to the interior receiving space;
removing the sanitizing module from the first container;
connecting the sanitizing module to the open end of the second container to enclose the interior receiving space whereby the at least one ultraviolet light emitting element emits ultraviolet light from the housing and into the interior receiving space of the second container when the sanitizing module is connected to the second container;
wherein the first container has a tapered prism shape that increases in cross-sectional area moving from the open end towards a bottom end opposite the open end;
wherein the first container has a non-circular cross-section and four sidewalls that are flat;
wherein the second container has at least one of a different size, material construction and/or shape than the first container; and
wherein the housing is dome-shaped and includes a plurality of protrusions arranged in an annular configuration on an exterior surface of the housing distal from the open end, the plurality of protrusions enabling gripping of the housing by a palm of a hand of a user.

16. The method according to claim 15, wherein:
the sanitizing module is configured to emit the ultraviolet light into the interior receiving space automatically when the sanitizing module is connected to the first container or the second container.

17. The sanitizing container system of claim 15, wherein:
at least one of the first container and the second container has an interior surface comprising a reflective material.

* * * * *